(12) United States Patent
Hibert et al.

(10) Patent No.: US 7,745,413 B2
(45) Date of Patent: Jun. 29, 2010

(54) COLLECTION OF TRACEABLE COMPOUNDS AND USES THEREOF

(75) Inventors: Marcel Francois Louis Hibert, Eschau (FR); Christel Anne Franchet, Holtzheim (FR); Jean-Luc Galzi, Weitbruch (FR); Franc Emile Jean Pattus, Brussels (BE); Fabrice Yves Guillier, Geispolsheim (FR)

(73) Assignees: Centre National de la Recherche Scientifique (CNRS), Paris (FR); Universite Louis Pasteur, Strasbourg (FR)

( * ) Notice: Subject to any disclaimer, the term of this patent is extended or adjusted under 35 U.S.C. 154(b) by 380 days.

(21) Appl. No.: 11/597,891

(22) PCT Filed: Jun. 15, 2005

(86) PCT No.: PCT/FR2005/001501

§ 371 (c)(1),
(2), (4) Date: Mar. 13, 2007

(87) PCT Pub. No.: WO2006/003329

PCT Pub. Date: Jan. 12, 2006

(65) Prior Publication Data

US 2008/0176763 A1      Jul. 24, 2008

(30) Foreign Application Priority Data

Jun. 15, 2004   (FR) ................... 04 06465

(51) Int. Cl.
*A61K 38/00*   (2006.01)
*A61K 31/4965*   (2006.01)
*C40B 40/04*   (2006.01)

(52) U.S. Cl. .................. 514/19; 514/255.01; 506/15
(58) Field of Classification Search ................. None
See application file for complete search history.

(56) References Cited

U.S. PATENT DOCUMENTS

2007/0249013 A1* 10/2007 Hibert et al. .................. 435/34
2008/0176763 A1*  7/2008 Hibert et al. .................. 506/15

FOREIGN PATENT DOCUMENTS

FR      2841246        12/2003
WO      WO9949067   *   9/1999
WO      02/072613       9/2002

OTHER PUBLICATIONS

Ciolina et al. Coupling of Nuclear Localization Signals to Plasmid DNA and Specific Interaction of the Conjugates with Importin alpha. Bioconjugate Chem 1999. vol. 10, pp. 49-55.*

* cited by examiner

*Primary Examiner*—Cecilia Tsang
*Assistant Examiner*—Marcela M Cordero Garcia
(74) *Attorney, Agent, or Firm*—Young & Thompson

(57) ABSTRACT

The use of a collection of compounds of general formula (I), wherein: n is 0 or 1; p represents an integer between 1 and 6; r represents an integer between 1 and 12; $R_1$ and $R'_1$ represent in particular a hydrogen atom; $R_2$ represents an amino acid side chain or an amino acid derivative; $R_3$ represents a group derived from a carboxylic acid, bearing a basic entity; $R_4$ represents in particular an alkyl group containing 1 to 10 carbon atoms; and A represents a hydrogen atom, a protecting group or a tracing group, in particular a fluorophor, a coloring agent or a quencher, for determining, through binding studies, ligands of receptors whose ligand is unknown or whose ligand useful for carrying out specific affinity binding assays is unknown.

24 Claims, 7 Drawing Sheets

COLLECTION OF TRACEABLE COMPOUNDS AND USES THEREOF

A subject of the present invention is collections of traceable compounds, in particular of fluorescent compounds, as well as uses thereof, in particular within the framework of the determination of ligands of a receptor no ligand of which is known or no ligand of which is known that can be used for specific affinity binding studies.

The gene coding for a fluorescent protein originating from the jelly fish *Aequorea victoria*, green fluorescent protein (or GFP) has been sequenced by Prasher et al. (*Gene*, 1992, 111:229-233). GFP is a monomeric protein. It acquires its fluorescence properties by an autocatalytic fluorophore formation mechanism.

Numerous medicaments and natural substances perform their action by interacting with regulating proteins called receptors, involved in numerous physiological functions of organisms, and the alterations of their functions are the cause of numerous pathologies. The receptors' accessibility to natural or synthetic, endogenous or exogenous pharmacological agents from outside the cell leads to their being considered as targets of choice for research into biologically active molecules, in particular molecules having potential therapeutic powers.

The sequencing of the human genome gives access to the sequence of hundreds of novel proteins neither the endogenous ligand nor the biological function of which are known. These so-called "orphan" proteins constitute potential sites for the action of medicaments.

The methods existing at present make it possible to detect only agonist molecules which activate a function associated with the protein. This type of functional test leads to numerous false positives which are costly in terms of time and money. Moreover, the antagonist molecules which would inhibit the function associated with the protein cannot be detected directly by these methods. The antagonists have the best therapeutic potential most of the time.

The purpose of the present invention is to propose a method for the determination of any ligand, whether endogenous or exogenous, making it possible to do without a systematic search for the endogenous or natural ligand.

One of the aims of the invention is to provide a screening method for determining the first ligands of an orphan receptor without knowing its endogenous ligand.

The present invention relates to the use of a collection of compounds corresponding to the following general formula (I):

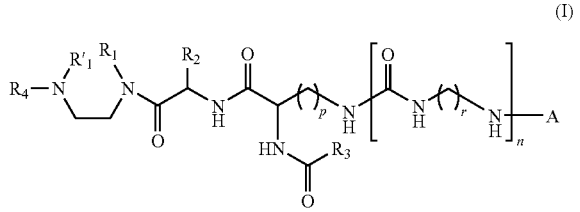

in which:

n is equal to 0 or 1, p represents an integer varying from 1 to 6, and is preferably equal to 4, r represents an integer varying from 1 to 12, and is preferably equal to 4, $R_1$ and $R'_1$ represent independently of each other a hydrogen atom, an alkyl group comprising from 1 to 6 carbon atoms, or an aromatic group, in particular a benzyl group or a phenethyl group, optionally substituted by a halogen atom, a methoxy group or an alkyl group comprising from 1 to 6 carbon atoms, or $R_1$ and $R'_1$ can form a ring comprising from 2 to 4 carbon atoms, in particular 2 carbon atoms, $R_2$ represents a side chain of an amino acid or an amino acid derivative, $R_3$ represents a group derived from a carboxylic acid, carrying a basic entity, in particular chosen from the following groups:

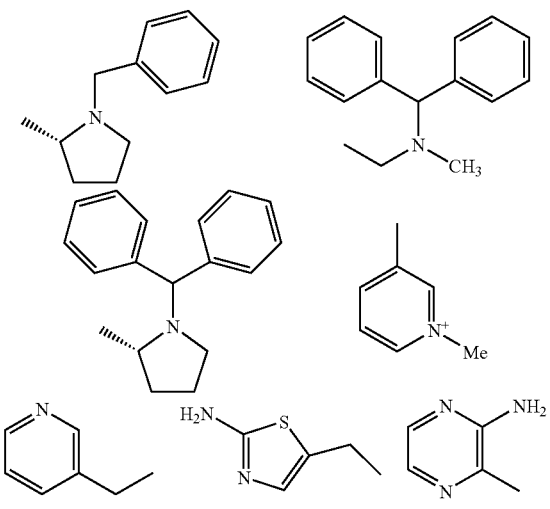

$R_4$ represents an alkyl group comprising from 1 to 10 carbon atoms, in particular from 1 to 6 carbon atoms, a phenyl group substituted by an alkyl group comprising from 1 to 10 carbon atoms, in particular from 1 to 6 carbon atoms, $R_4$ preferably being a methyl group, a benzyl group or an allyl group, and A represents a hydrogen atom, a protective group or a tracer group, in particular a fluorophore, a dye or a "quencher", for the in vitro determination, by binding studies, of ligands of receptors no ligand of which is known or no ligand of which is known that can be used in order to carry out specific affinity binding studies.

The expression "collection of compounds" designates a set of molecules which can be prepared according to a common protocol.

The expression "tracer group" designates a fluorescent chemical entity or a chemical entity possessing properties of staining or absorption of certain wavelengths.

The expression "receptor no ligand of which is known" designates any biological macromolecule ("receptor") for which no endogenous or exogenous molecules binding to it in reversible manner are known.

The expression "specific affinity binding test" designates the measurement of the interaction force between two molecules, namely a receptor and its ligand.

The present invention involves the design, synthesis and screening of collections of fluorescent molecules on receptors themselves made fluorescent in particular by fusion to the green fluorescent protein GFP.

The present invention also relates to a compound of the following formula (I):

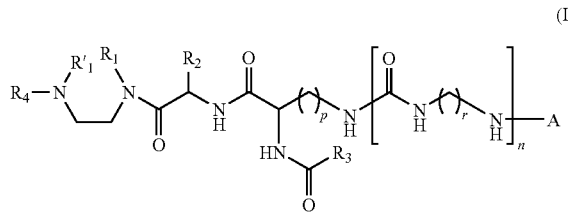

in which:

n is equal to 0 or 1,
p represents an integer varying from 1 to 6, and is preferably equal to 4,
r represents an integer varying from 1 to 12, and is preferably equal to 4,
$R_1$ and $R'_1$ represent independently of each other a hydrogen atom, an alkyl group comprising from 1 to 6 carbon atoms, or an aromatic group, in particular a benzyl group or a phenethyl group, optionally substituted by a halogen atom, a methoxy group or an alkyl group comprising from 1 to 6 carbon atoms, or $R_1$ and $R'_1$ can form a ring comprising from 2 to 4 carbon atoms, in particular 2 carbon atoms,
$R_2$ represents a side chain of an amino acid or an amino acid derivative,
$R_3$ represents a group derived from a carboxylic acid, carrying a basic entity, in particular chosen from the following groups:

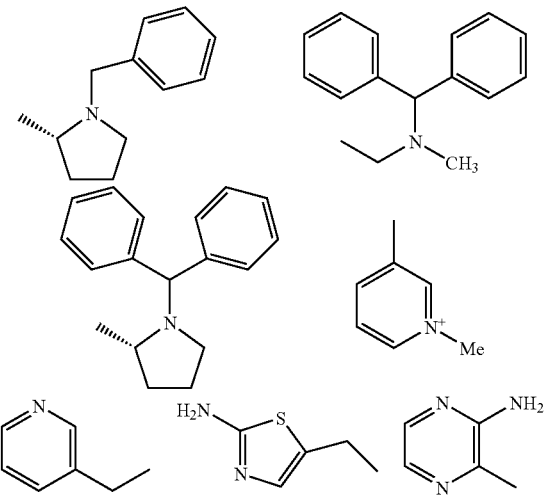

$R_4$ represents an alkyl group comprising from 1 to 10 carbon atoms, in particular from 1 to 6 carbon atoms, a phenyl group substituted by an alkyl group comprising from 1 to 10 carbon atoms, in particular from 1 to 6 carbon atoms, $R_4$ preferably being a methyl group, a benzyl group or an allyl group, and
A represents a hydrogen atom, a protective group or a tracer group, in particular a fluorophore, a dye or a "quencher".

The present invention relates to a compound of formula (I) as defined above, characterized in that $R_2$ represents the side chain of an amino acid or amino acid derivative chosen from the group comprising: alanine, glutamine, leucine, glycine, tryptophan, β-alanine, phenylalanine, 4-chloro-phenylalanine, isonipecotinic acid, 4-aminomethylbenzoic acid, 3-tetrahydroisoquinolinic acid and free or benzylated histidine.

More precisely, the amino acid or amino acid derivative the side chain of which corresponds to $R_2$ is chosen from:

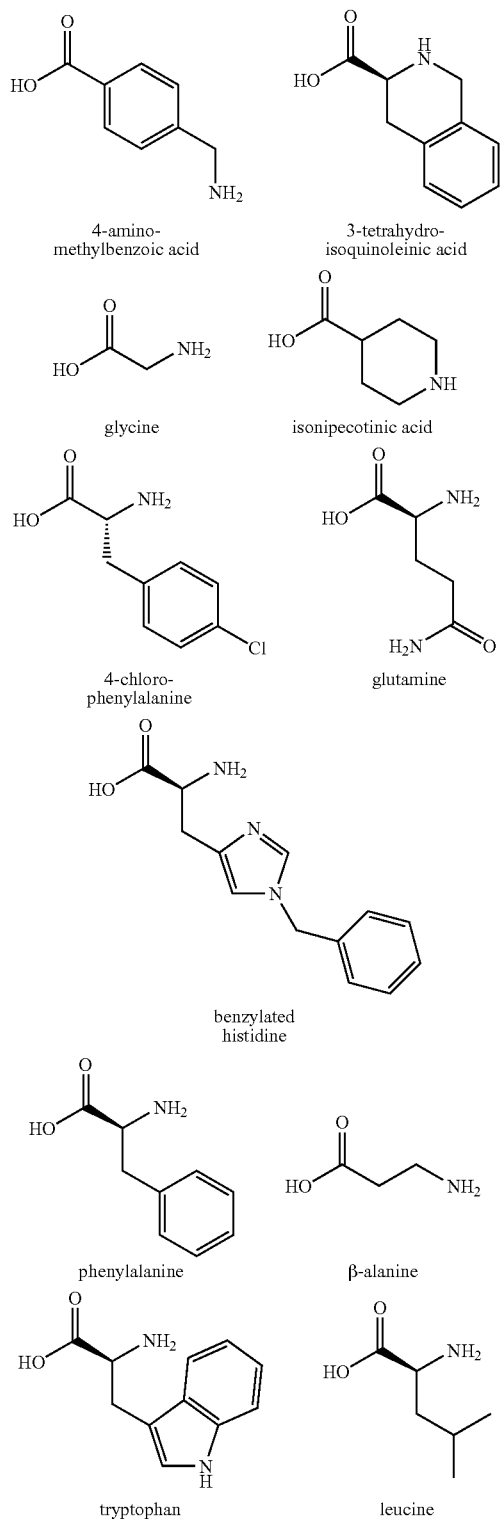

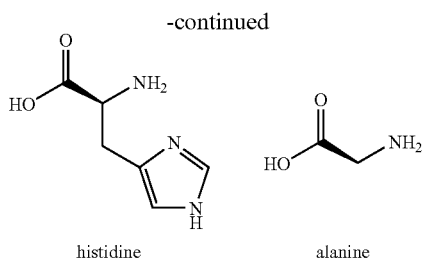

histidine    alanine

An advantageous compound according to the invention is a compound of formula (I) as defined previously in which n is equal to 0.

Such a compound corresponds to the following formula (I-a):

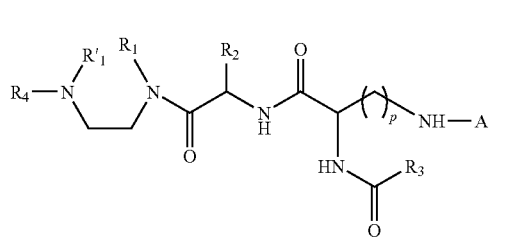

(I-a)

Such a compound is advantageous to the extent that it has a low molecular mass.

An advantageous compound according to the invention is a compound of formula (I) as defined previously in which n is equal to 1.

Such a compound corresponds to the following formula (I-b):

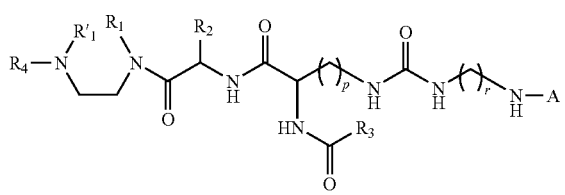

(I-b)

Such a compound is advantageous to the extent that it has a low molecular mass.

An advantageous compound according to the invention is a compound of formula (I-a) as defined above, characterized in that A represents a hydrogen atom or a protective group (GP), in particular a Boc group.

Such a compound corresponds to one of the following formulae:

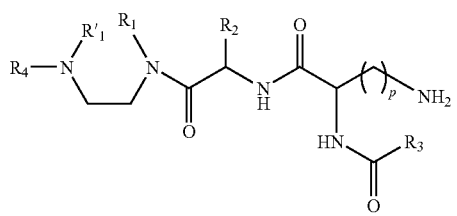

According to an advantageous embodiment of the present invention, the present invention relates to a compound as defined above corresponding to one of the following formulae:

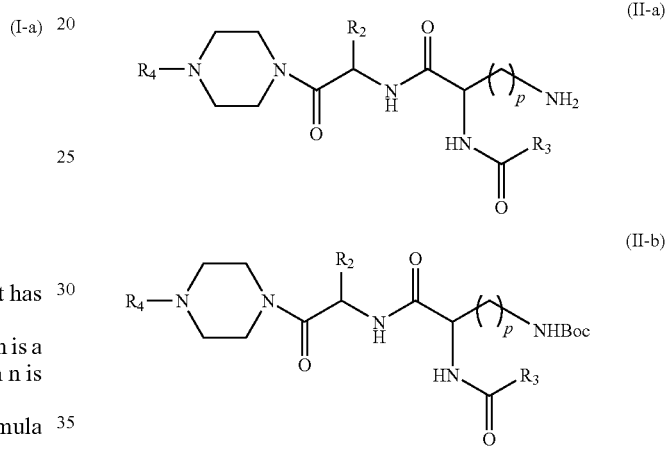

(II-a)

(II-b)

in which $R_2$, $R_3$, $R_4$ and p are as defined above, p preferably being equal to 4.

The abovementioned compounds of formula (II-a) or (II-b) are advantageous to the extent that they have piperazine units, carrying biological activity.

The present invention also relates to a compound as defined above, of formula (I-a) or (I-b), characterized in that A represents a fluorophore group chosen from the group comprising Bodipy and lissamine derivatives.

According to an advantageous embodiment, the compounds of the invention of formula (I-a) or (I-b) are characterized in that A represents one of the following groups:

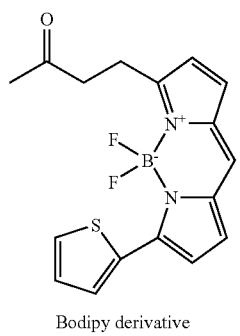

Bodipy derivative

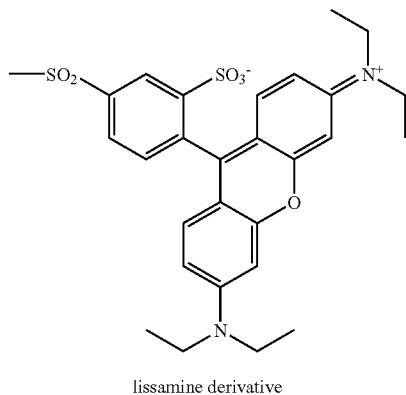

lissamine derivative

A particularly advantageous compound according to the invention is a compound as defined above, corresponding to the following formula (III):

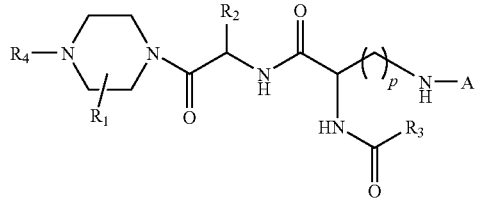

in which:

R$_1$, R$_2$, R$_3$, R$_4$ and p are as defined above in formula (I), and

A is as defined above, i.e. it represents a fluorophore group chosen from the Bodipy and lissamine derivatives.

According to an advantageous embodiment of the invention, the present invention relates to a compound of formula (III), characterized in that p=4 and corresponding to the following formula:

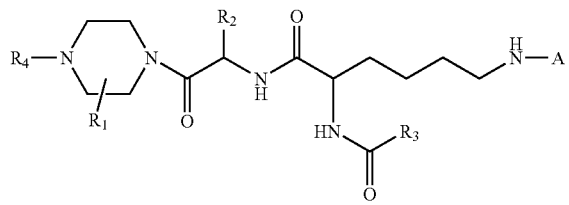

in which R$_1$, R$_2$, R$_3$ and R$_4$ are as defined above.

The present invention also relates to a compound as defined above, corresponding to the following formula (III-a):

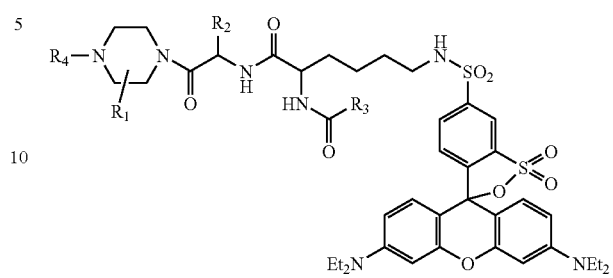

in which R$_1$, R$_2$, R$_3$ and R$_4$ are as defined above.

A particularly advantageous compound according to the invention is a compound as defined above, corresponding to the following formula (IV):

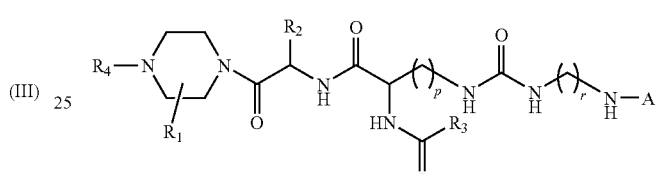

in which R$_1$, R$_2$, R$_3$, R$_4$, A, p and r are as defined above.

An advantageous compound of the invention is a compound of the abovementioned formula (IV) in which p=4, and corresponding to the following formula:

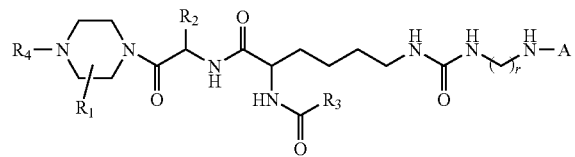

An advantageous compound of the invention is a compound of the abovementioned formula (IV) in which r=4, and corresponding to the following formula

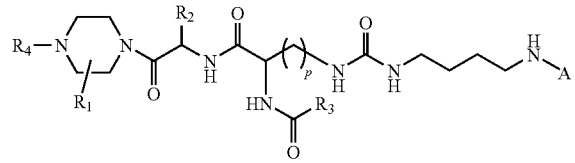

An advantageous compound of the invention is a compound of the abovementioned formula (IV) in which p and r are equal to 4, and corresponding to the following formula:

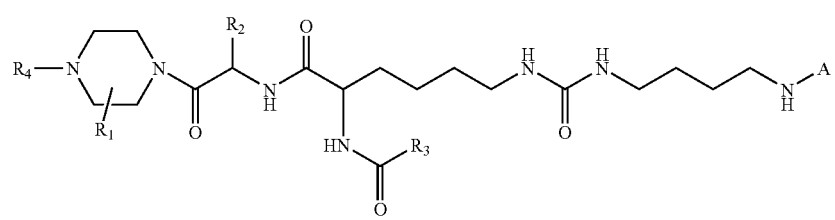

An advantageous compound of the invention is a compound as defined above, corresponding to the following formula (IV-a):

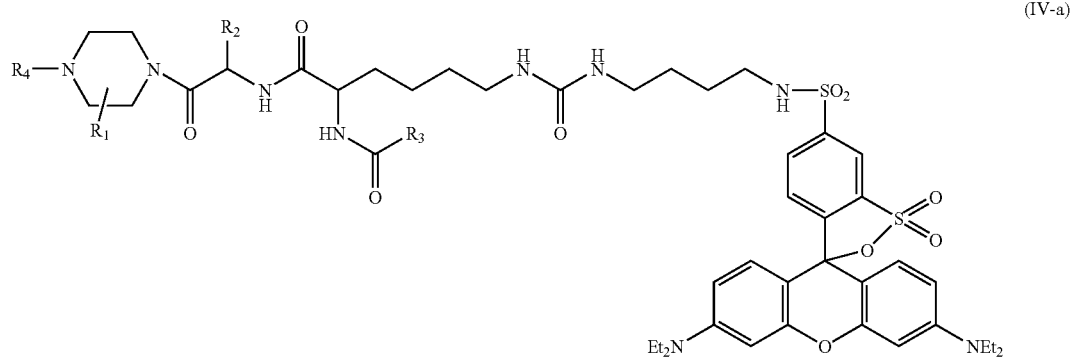

(IV-a)

in which $R_1$, $R_2$, $R_3$ and $R_4$ are as defined above.

The present invention also relates to a collection comprising a plurality of compounds as defined above.

The expression "collection" designates all of the molecules which can be prepared according to a common protocol.

The present invention also relates to a collection comprising a plurality of compounds as defined above, corresponding to formula (III-a).

The present invention also relates to a collection comprising a plurality of compounds as defined above, corresponding to formula (IV-a).

The present invention also relates to the use of a collection as defined above, for the in vitro determination, by binding studies, of ligands of receptors no ligand of which is known or no ligand of which is known that can be used for carrying out specific affinity binding studies.

The present invention relates to a method of screening of ligands of receptors no ligand of which is known or no useable ligand of which is known, said method comprising the following stages:
  bringing a collection of traceable compounds according to the invention together with cells transfected by a construction containing the fusion of the sequence coding for a fluorescent protein with the nucleotide sequence coding for a receptor no ligand of which is known or no useable ligand of which is known, and the mixture of said cells and of said collection,
  detection of the fluorescence of said mixture, by excitation of said fluorescent protein and measurement of the emission fluorescence of said fluorescent protein, and determination of the fluorescence extinction percentage by comparing the emission fluorescence of said fluorescent protein in the mixture to the average fluorescence of said fluorescent protein in the absence of ligand,
  the average fluorescence of said fluorescent protein being measured by control tests corresponding to the measurement of the fluorescence of the fluorescent protein in the absence of the collection of compounds, and
  determination of the compounds which produce a fluorescence extinction percentage of the fluorescent protein of at least 5% and their identification as ligand.

The present invention relates more particularly to a method for screening ligands of G-protein-coupled receptors (GPCR) such as GPR50, GPR37, GPR19, GPR15, GPR31, GPR81, GPR3 and EDG7, the receptor APJ, FPRL1, the chemokine receptors CXCR1, CXCR2, CXCR3, CXCR4, the Glucagon-like peptide receptors (GLP-1R and GLP-2R), the CRF1 and CRF2 receptors, the metabotropic glutamate receptors (mGluR) and the GABA receptors.

The present invention also relates to a method for screening GPCR ligands no ligand of which is known, such as the orphan receptors GPR50, GPR37, GPR19, GPR31, GPR81, GPR3 and EDG7.

The present invention also relates to a method for screening GPCR ligands no ligand of which is known that can be used according to the method of the invention, such as the APJ receptor, the FPRL1 receptor, the chemokine receptors, CXCR1, CXCR2, CXCR3, CXCR4, the Glucagon-like peptide receptors (GLP-1R and GLP2-R), CRF1, CRF2, the metabotropic glutamate receptors (mGluR) and the GABA receptors.

The present invention relates to a preparation method on solid support of a compound of formula (I), characterized in that it comprises the following stages:
  the coupling of a solid support of formula

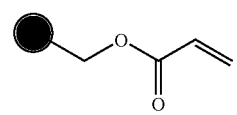

to a compound of formula

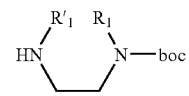

in order to obtain a compound of the following formula (1):

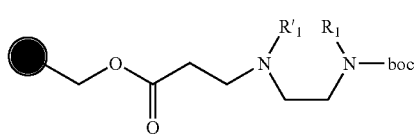

$R_1$ and $R'_1$ being as defined above, the deprotection of the compound of formula (1) followed by the coupling of said deprotected compound to the compound of formula

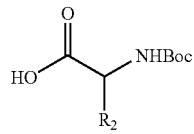

in order to obtain a compound of the following formula (2):

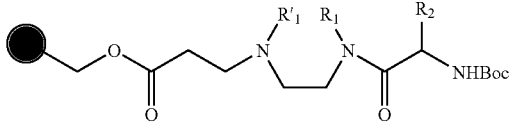

$R_2$ being as defined above, the deprotection of the compound of formula (2) followed by the coupling of said deprotected compound with the compound of formula

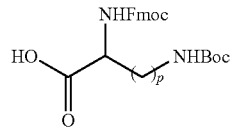

in order to obtain a compound of the following formula (3):

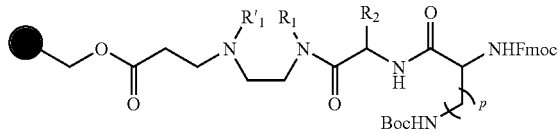

p being as defined above, the deprotection of the Fmoc group of the compound of formula (3) followed by the coupling of said deprotected compound to the compound $R_3COOH$ in order to obtain a compound of the following formula (4):

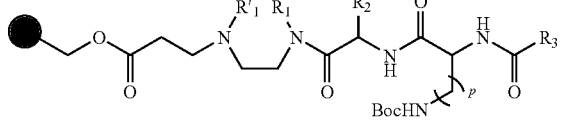

$R_3$ being as defined above, the deprotection of the compound of formula (4) in order to obtain a compound of the following formula (5):

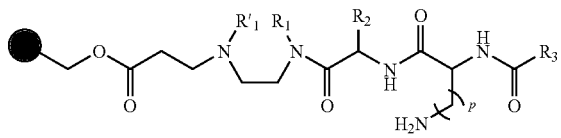

optionally the reaction of the compound of formula (5) with p-nitrophenylchloroformate then with diamine of formula

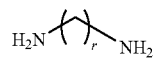

in order to obtain the compound of the following formula (6):

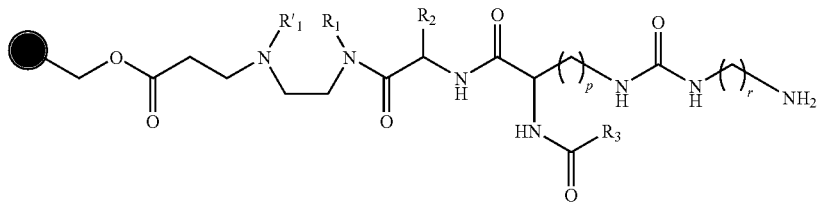

r being as defined above, the reaction of the compound of formula (5) or of the compound of formula (6) with electrophilic tracers, in particular with A-Cl, in order to obtain the compound of the following formula (7):

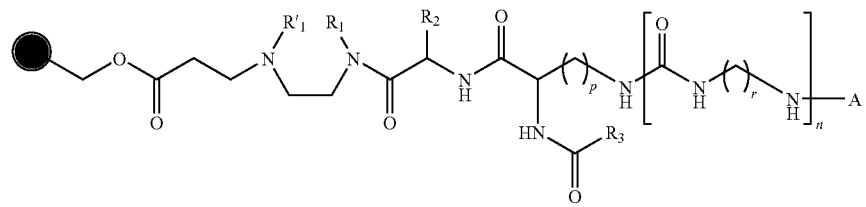

n being equal to 0 or 1,

A representing Bodipy in the form of activated acid or lissamine in the form of activated sulphonic acid, the cleavage of the compound of formula (7) with the compound $R_4X$, $R_4$ being as defined above, and X representing a halogen atom, in particular I or Br, in order to obtain a compound of formula (I) as defined above.

EXAMPLES

I—Development of the Synthesis

Figure 1:
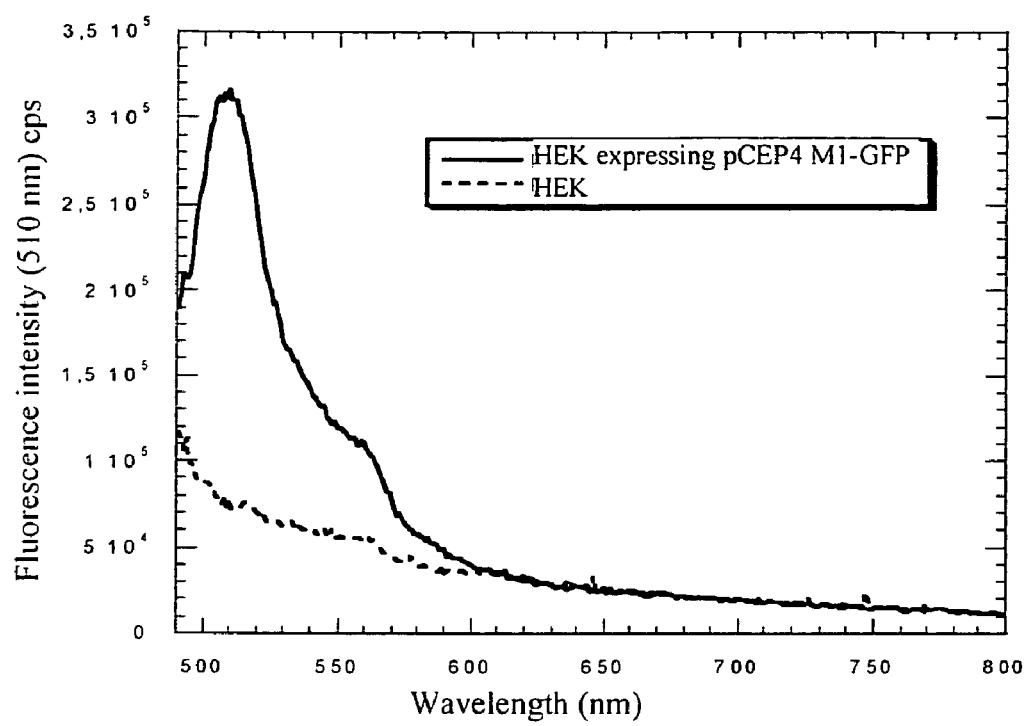
FIG. 1 represents an emission spectrum of HEK 293 cells transfected by the construction pCEP4-SP-EGFP-M1 (see Example 1 hereafter). The y-axis corresponds to the wavelength (in nm) and the x-axis to the fluorescence intensity (in cps). The solid-line curve corresponds to the HEK cells expressing pCEP4-SP-EGFP-M1 and the dotted-line curve to the non-transfected HEK cells

1. Choice of Support, Washing Conditions and Monitoring of the Reactions

REM 2 type resin is chosen for its ability to generate tertiary amines. The cleavage is carried out in 2 stages: activation and formation of ammonium by alkylation of tertiary amine followed by β-elimination in the presence of base (Morphy, J. R.; Rankovic, Z.; Rees, D. C. (1996) *Tetrahedron Lett.*, 37, 3209-3212; Brown, A. R.; Rees, D. C.; Rankovic, Z.; Morphy, J. R. (1997) *J. Am. Chem. Soc.*, 119, 3288-3295).

The standard techniques of synthesis on solid support are used. In particular, the resin is filtered then washed after each stage by repeating 3 times a standard DMF/DCM/MeOH sequence (5 to 10 ml per gram of resin) then DCM/MeOH/$Et_2O/Et_2O$ and finally dried under vacuum using a vane pump for at least 6 hours.

The monitoring of the reaction and the yield are determined after cleavage and weighing of the pure product after each stage of the synthesis (in general starting with 200 mg of resin i.e. approximately 0.1 to 0.2 mmol of product or 30 to 50 mg). During the first stages, the product is sufficiently pure and requires no purification procedure. As the synthesis proceeds, the impurity level increases and the product must be purified before determination of the yield. The yield is established relative to the theoretical load of the resin provided by the supplier.

The pseudo-purity is estimated by RP-HPLC at 220 nm or 254 nm. The purity analysis is carried out on an aliquot of 10 to 20 mg of resin i.e. 5 to 20 mmol (1 to 5 mg) of product.

The identification is carried out by MS after dilution of the HPLC analytical sample and by NMR $^1H$ and $^{13}C$ during the cleavages carried out on a larger scale during the determination of the yields.

The purity and identification can be obtained by NMR $^1H$ when the reaction is carried out on 50 mg of resin i.e. 25 to 50 µmol (5 to 15 mg) of product. This is generally the case in the development phase where the use of NMR is usual. For analysis flow-rate reasons, the use of HPLC and MS is preferred in the "building blocks" selection and combinatorial library analysis phases.

2. Michael Addition on REM Resin

REM resin 2 is prepared in accordance with the procedure in the literature (Diagram 1) from commercial hydroxymethylpolystyrene 1. It is assumed that the reaction is quantitative after a double coupling of 10 equivalents of acryloyl chloride [1 M] in DCM (10 ml per gram of resin). The qualitative analysis is carried out by IR and the appearance of the carbonyl frequencies (1720 $cm^{-1}$) and the α,β unsaturation (1403 $cm^{-1}$).

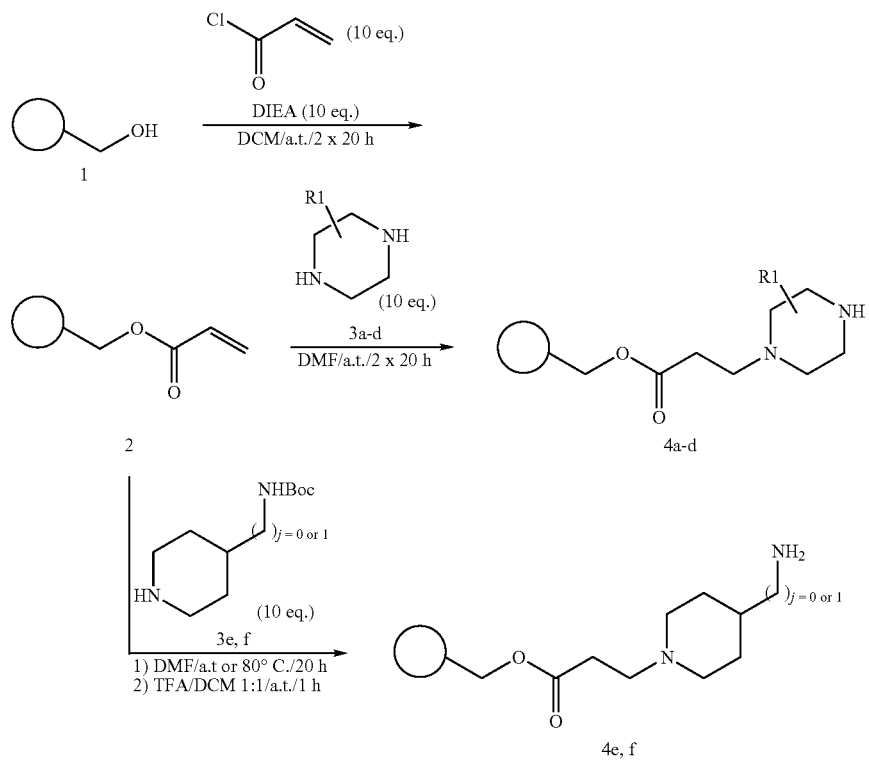

Diagram 1.

Michael addition on the acrylate 2 is carried out with 10 equivalents of secondary amines 3 in DMF by carrying out a double coupling thus providing access to the β-aminoester 4. An important factor is the amine concentration which must be high, close to 1 M (10 ml per gram of resin). When the amine is not commercially available, and therefore more difficult to access, a single coupling was carried out without any notable reduction in conversion. At high concentrations, certain amines must be heated in order to allow dissolution (3a, b, e, f). Thus, the reaction with 4-Boc-aminopiperidine 3e is carried out at 80° C. for reasons of solubilization of the amine.

The synthesis requires the use of diamines 3 (Table 1).

TABLE 1

| Diamines $R_1$ | 3a | 3b | 3c | 3d | 3e | 3f |
|---|---|---|---|---|---|---|
| Products | 13a | 13b | 13c | 13d | 13e | 13f |
| Yield (%) isolated pdt | 95 | 40 | 89 | 21 | 80 | 34 |
| HPLC (%) 220 nm | 86 | >95 | >95 | >95 | >95 | >95 |

When symmetrical diamines are used, a monoprotection is not necessary due to the principle of isolation of the sites by the solid support. In the case of use of asymmetrical amines, a monoprotection by the Boc group is carried out in regio- and chemoselective manner. Thus 4-Boc-aminopiperidine 3e and 4-Boc-aminomethylpiperidine 3f are obtained (Contreras, J. M.; Rival, Y. M.; Chayer, S.; Bourguignon, J. J.; Wermuth, C. G. (1999) *J. Med. Chem.*, 42, 730-741) (Diagram 2) starting with commercial 4-amino-1-benzylpiperidine and isonipecotamide respectively.

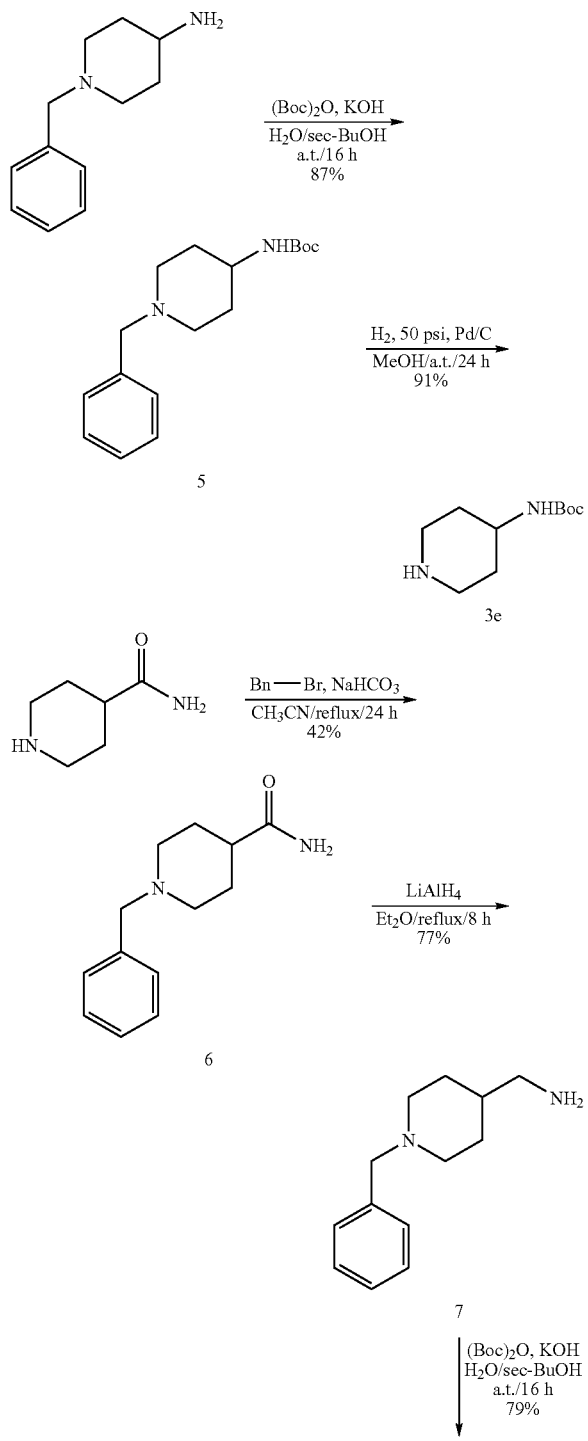

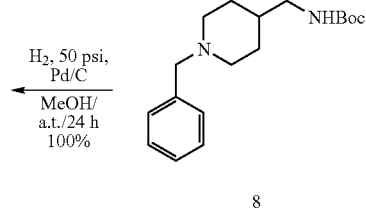

This type of mono-protected diamines requires a stage of deprotection of the Boc groups using TFA (Diagram 1). The standard protocol for deprotection with TFA involves a TFA/DCM mixture 50:50 for 1 hour at ambient temperature using a volume of 30 ml per gram of resin. In practice the resin is pre-expanded in dichloromethane (DCM) (⅓ of the total volume) then a TFA/DCM mixture 3:1 is added (⅔ of the total volume). After reaction, the resin is washed using 3 sequences of DMF/10% DIEA(DCM)/DCM/MeOH in order to neutralize the TFA salt. The excess amine can be recovered after filtration and evaporation of the DMF. Quantification of the load of resin 4 is carried out systematically, after coupling with Fmoc-Phe-OH, on an aliquot of 25 mg of resin, and carrying out an Fmoc test (Bunin, B. A. (1998) in "The Combinatorial Index", Academic Press, San Diego) observing the OD of the adduct fluorenone-piperidine at 301 nm. The resins 4 are thus ready for the derivatization.

3. Coupling of Boc-Protected Amino Acids to the Supported Amine

Due to the well-established standard conditions for the coupling of Boc-protected amino acids 9 to a supported amine (standard C to N peptide synthesis), no particular development was carried out (Diagram 3). For considerations of solubilization of a large number of amino acids, the DMF is used pure although there are no risks of racemization of the amino acid. In a standard manner 3 equivalents of activated acid are used [0.1 M] in the DMF (30 ml per gram of resin). Due to a significant steric hindrance, certain amino acids are used in larger quantities (6 equivalents). In any case, the acids are preactivated in the form of HOBt esters, by stirring the acid with HOBt for 15 minutes then adding DIC and continuing stirring for another 15 minutes. Only then is the preactivated acid added to the amine on solid phase (previously expanded in DMF or DCM). The resins 4 are thus converted to resins 10.

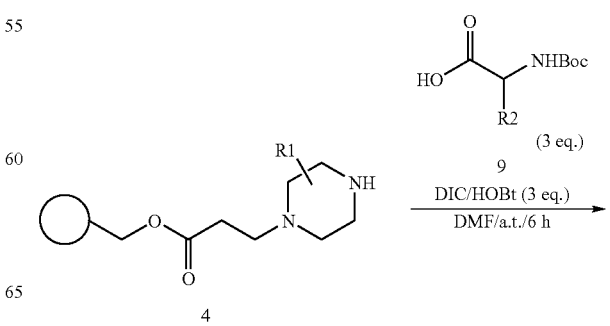

In order to increase the diversity of the "building blocks", a certain number of Boc-protected amino acids 9 were synthesized from commercial amino acids, due to the prohibitive cost or non-availability of the Boc-protected derivatives. A general method is described in Diagram 4. (Smith, J., Liras, J. L.; Schneider, S. E.; Anslyn, E. V. (1996) *J. Org. Chem.*, 61, 8811-08818; Huang, W.; Kalivretenos, A. G. (1995) *Tetrahedron Lett.*, 36, 9113-9116; Johnson, R. J.; Rajakumar, G.; Yu, K-L.; Mishra, R. K. (1986) *J. Med. Chem.*, 29, 2104-2107; Millington, C. R.; Quarrell, R.; Lowe, G. (1998) *Tetrahedron Lett.*, 39, 7201-7204; Khalil, E. M.; Subasinghe, N. L.; Johnson, R. L. (1996) *Tetrahedron Lett.*, 37, 3441-3444; Bukholder, T. P.; Kudlacz, E. M.; Maynard, G. D.; Liu, X-G.; Le, T-B.; et al. (1997) *Bioorg Med. Chem. Lett.*, 7, 2531).

4. Coupling of the Orthogonal Platform: Fmoc-Lys(Boc)-OH and Basic Carboxylic Acids $R_3$ The Boc protective group of the resin 10 (see Diagram 3) is treated with TFA according to the conditions described previously. The conditions for coupling of the Fmoc-Lys(Boc)-OH are standard and 3 equivalents of activated acid are used in DMF at ambient temperature over 6 hours (Diagram 5). The preactivation of the acid is carried out in the usual manner (DIC/HOBt). The orthogonal platform 14 is thus accessed.

After cleavage under standard conditions using DIEA and carrying out aqueous washing, the product 15a is obtained with a yield of 67%.

Diagram 5
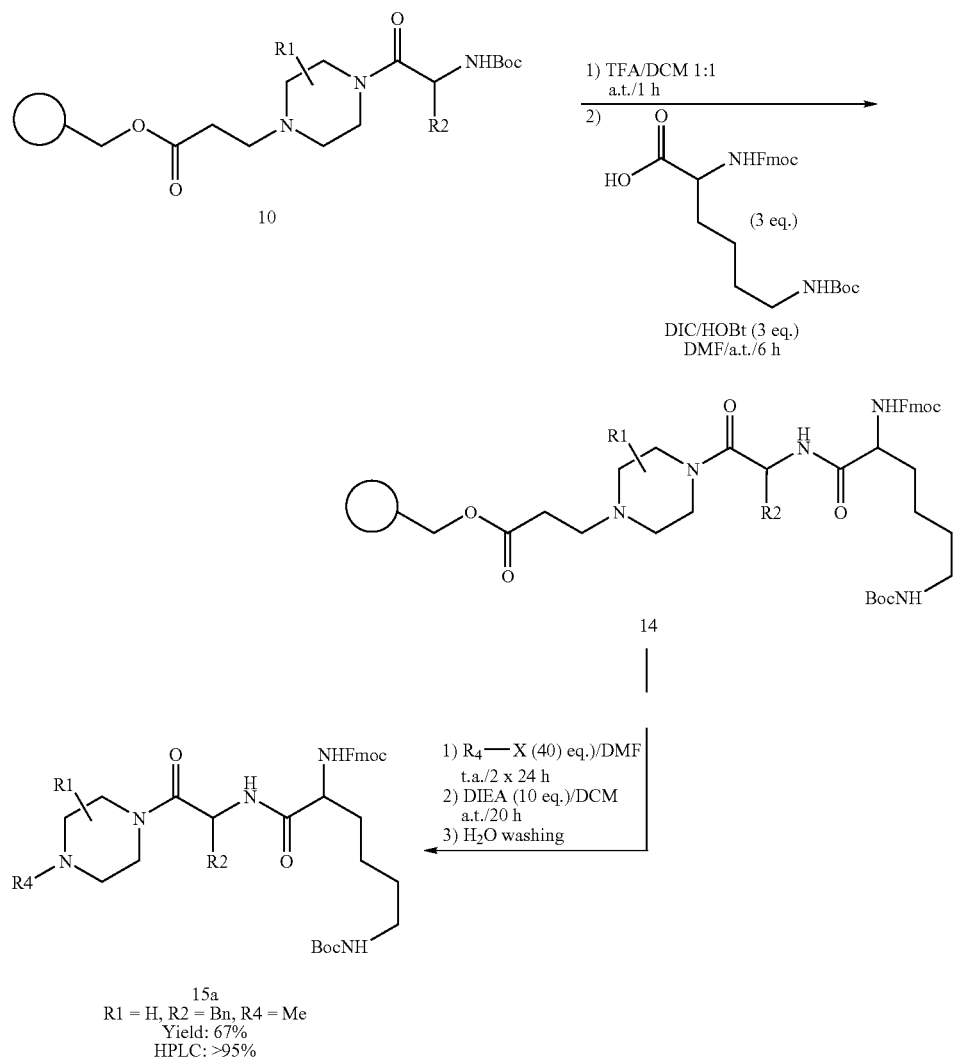
The selective deprotection of the Fmoc group on the resin 14 is carried out by using a mixture of 20% piperidine in DMF (20 ml per gram of resin) for 30 minutes and repeating this deprotection stage. This reaction is quantitative and the presence of residual Fmoc group has never been observed.
Diagram 6
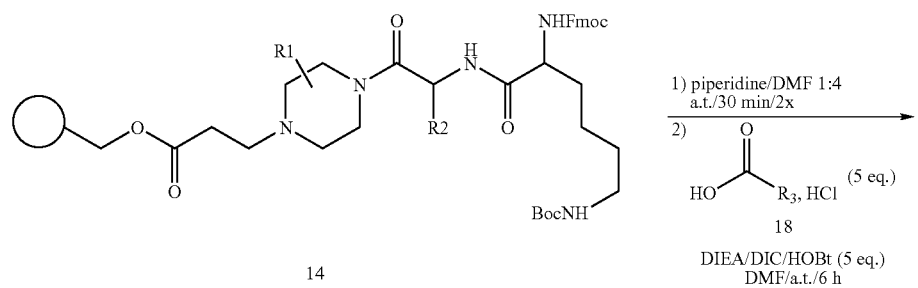

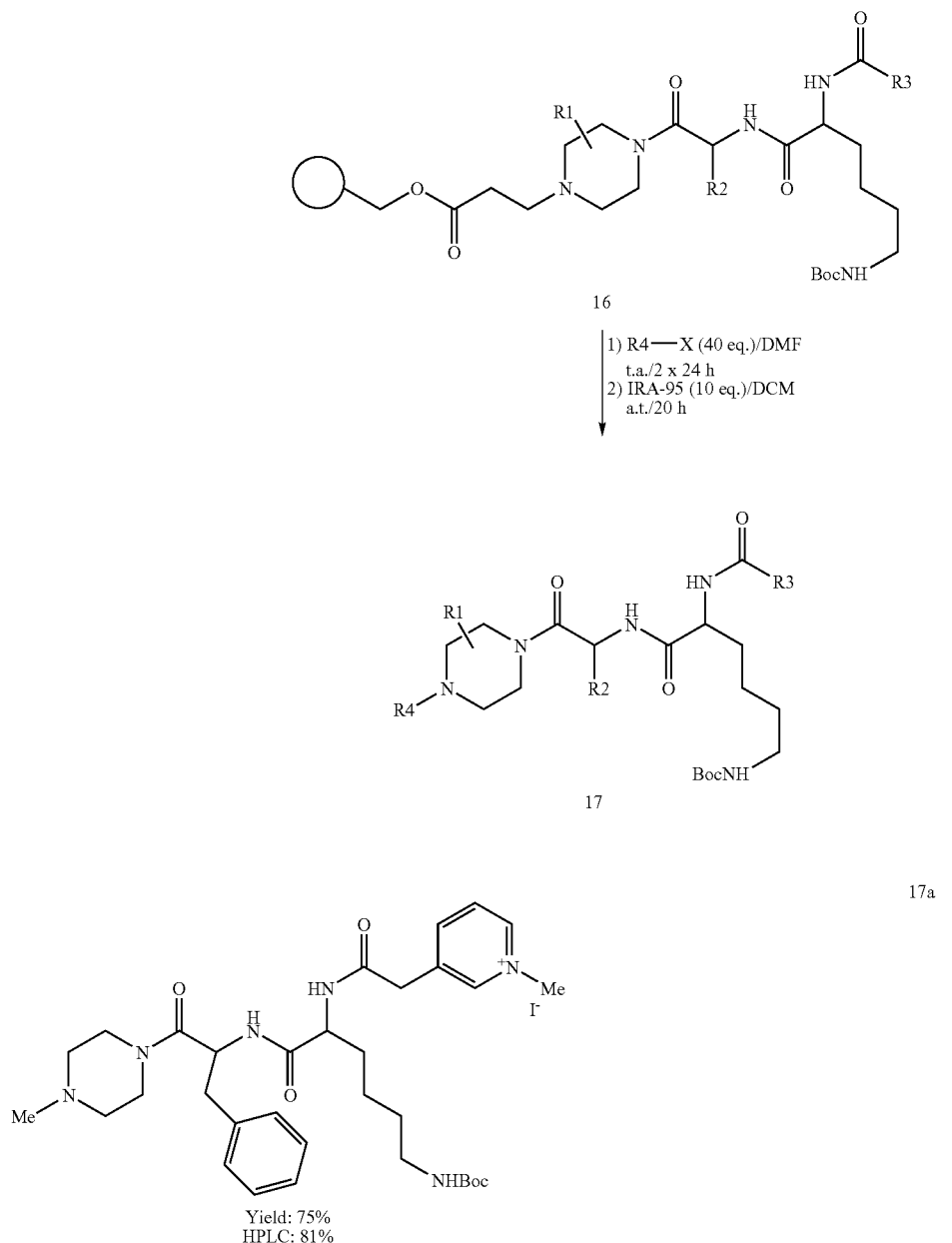

16

1) R4—X (40 eq.)/DMF
   t.a./2 x 24 h
2) IRA-95 (10 eq.)/DCM
   a.t./20 h

17

17a

Yield: 75%
HPLC: 81%

The preactivation of the acid from which $R_3$ derives is carried out in the usual manner (DIC/HOBt). The reaction thus leads to the structure 17 after cleavage, which constitutes the basis of the "white" version of the combinatorial library (without fluorophores) (Diagram 6). In fact, the other pre-cleavage stages from now on involve only the incorporation of the fluorophore.

A certain number of the carboxylic acids from which $R_3$s derive are available in the form of the hydrochloride due to their basicity. The reaction then requires the addition of DIEA. This time the use of DMF is crucial as numerous acids have been able to be selected due to a low solubility (even in the presence of DIEA and in hot DMF). This time, a slightly larger quantity of preactivated acid is used (5 equivalents).

The product 17a is obtained with a yield of 75% after cleavage, this time using the resin IRA-95. The purity of the crude product is estimated at 81% by HPLC at 220 nm, the impurities being essentially constituted by residual salts of $R_3$N.HI.

A certain number of carboxylic acids from which $R_3$s derive were synthesized so as to increase diversity in this position (Diagram 7). Thus the amino acids 18a, b, c are obtained from proline or sarcosine (Belokon, Y. N.; Tarasov, V. I.; Maleev, V. I.; Savel'eva, T. F.; Ryskov, M. G. (1998) *Tetrahedron: Asymetrie*, 9, 4249-4252), and the arecaidine 18d is obtained from commercial arecoline (Martin, A. R.; Paradkar, V. M.; Peng, G. W.; Speth, R. C.; Yamamura, H. I.; Horn, A. S. (1980) *J. Med. Chem.*, 23, 865-873).

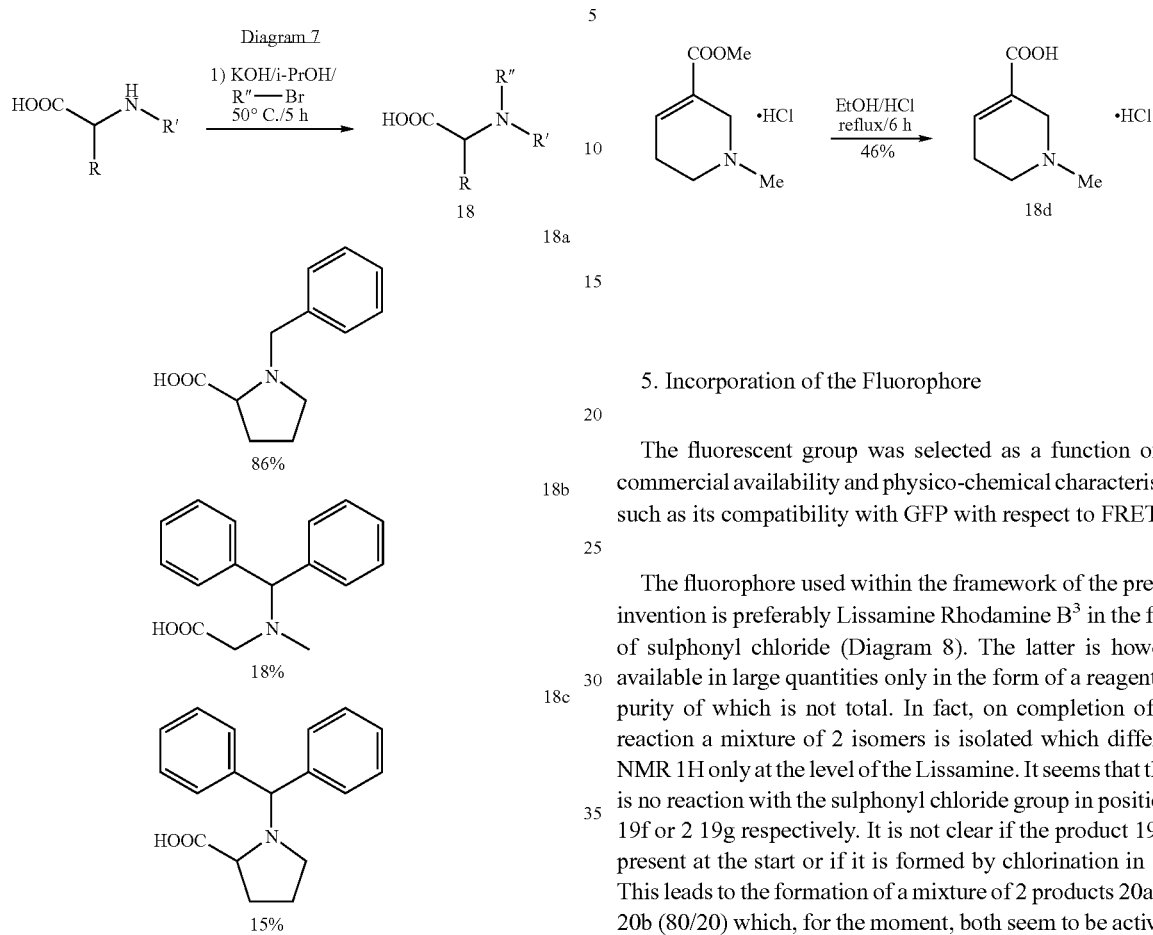

5. Incorporation of the Fluorophore

The fluorescent group was selected as a function of its commercial availability and physico-chemical characteristics such as its compatibility with GFP with respect to FRET.

The fluorophore used within the framework of the present invention is preferably Lissamine Rhodamine B[3] in the form of sulphonyl chloride (Diagram 8). The latter is however available in large quantities only in the form of a reagent the purity of which is not total. In fact, on completion of the reaction a mixture of 2 isomers is isolated which differ by NMR 1H only at the level of the Lissamine. It seems that there is no reaction with the sulphonyl chloride group in position 4 19f or 2 19g respectively. It is not clear if the product 19g is present at the start or if it is formed by chlorination in situ. This leads to the formation of a mixture of 2 products 20a and 20b (80/20) which, for the moment, both seem to be active in the FRET test.

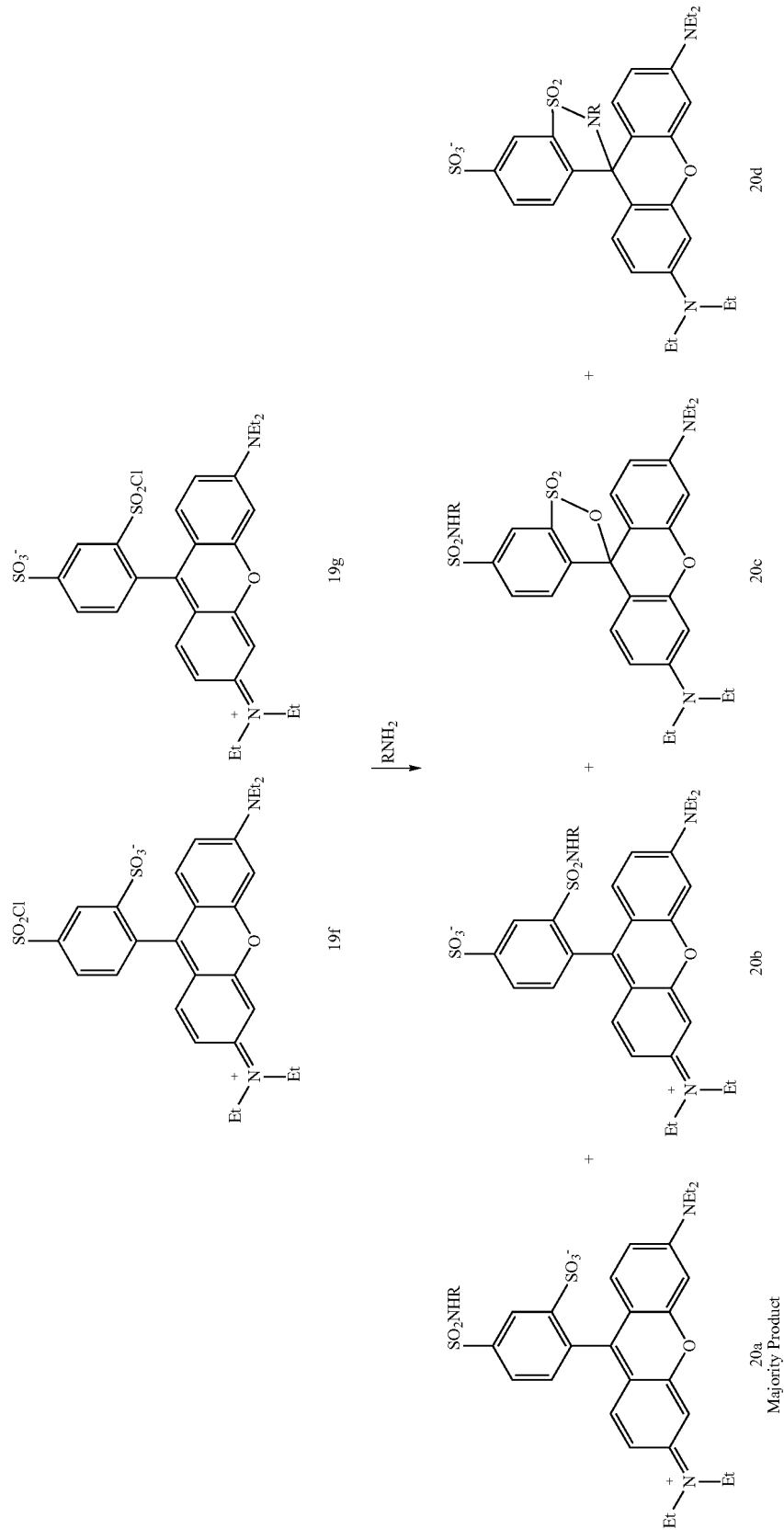

The incorporation of the fluorophore is carried out at the level of the lysine side chain on the amine in position $\epsilon$ after deprotection of the Boc group with TFA under the usual conditions (Diagram 9).

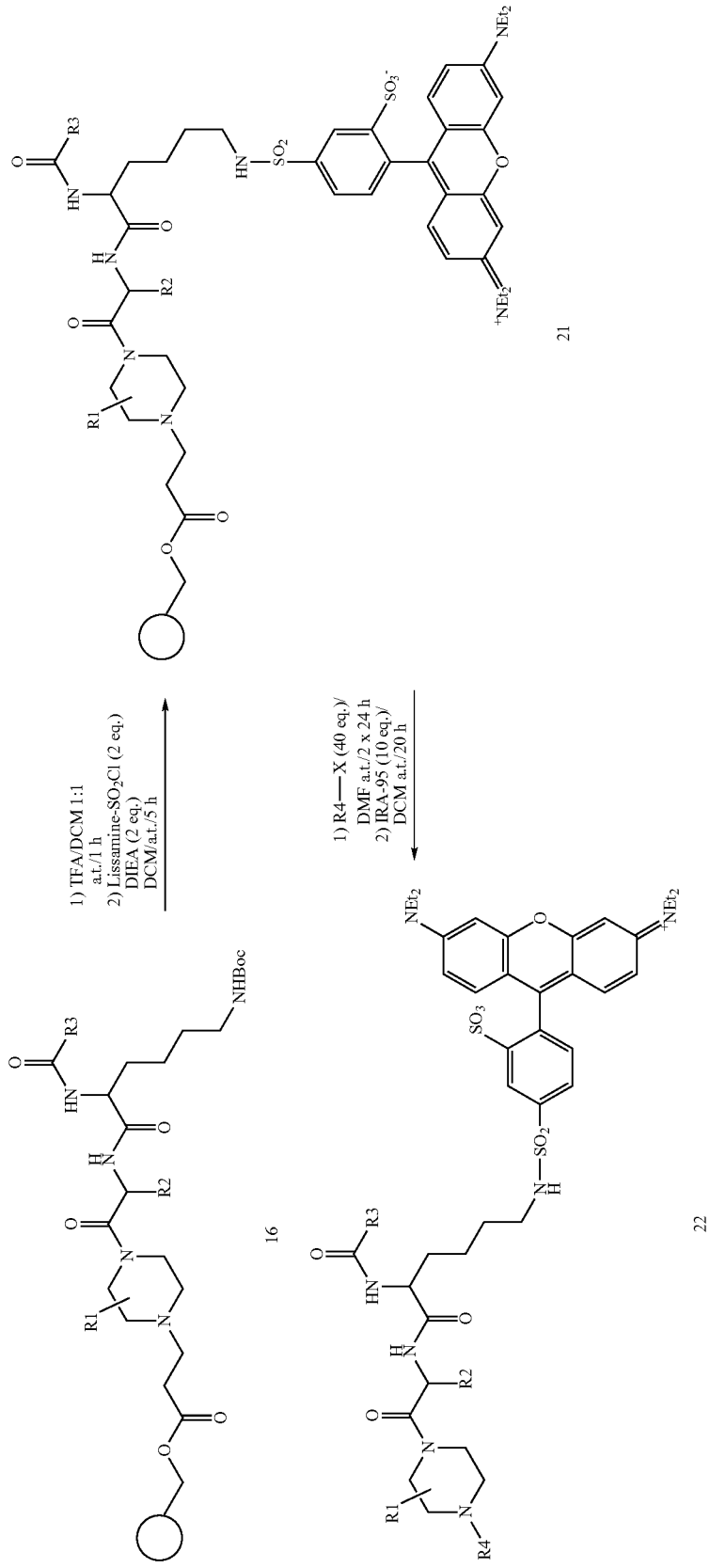
Diagram 9

After standard cleavage, the fluorescent compounds 22 are accessed from the supported compounds 21 (Diagram 9).

The compounds 22a, b, c are thus obtained after cleavage of the resin 21 using methyl iodide or benzyl bromide and the resin IRA95 as base, followed by purification by reversed-phase semi-preparative HPLC with respective overall yields of 25, 20 and 27% (Diagram 10). These products are accompanied by approximately 5-6% of the substitution isomer of the sulphonyl chloride group in position 2 of the lissamine.

Diagram 10

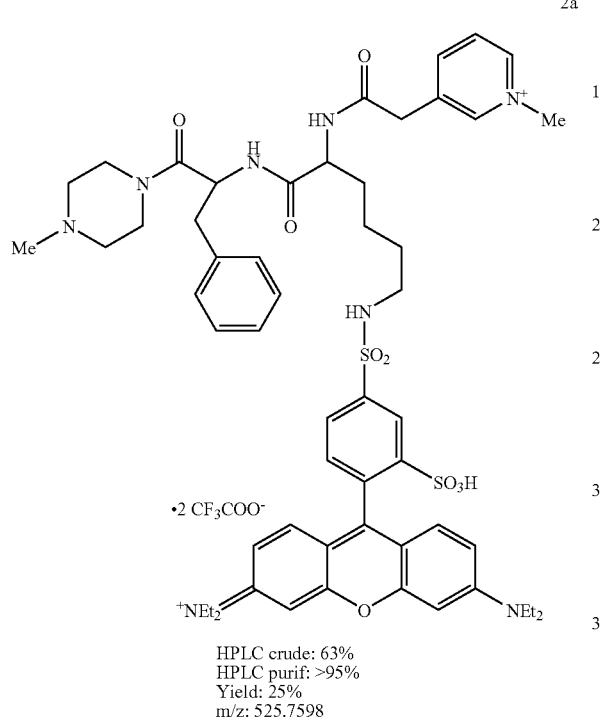

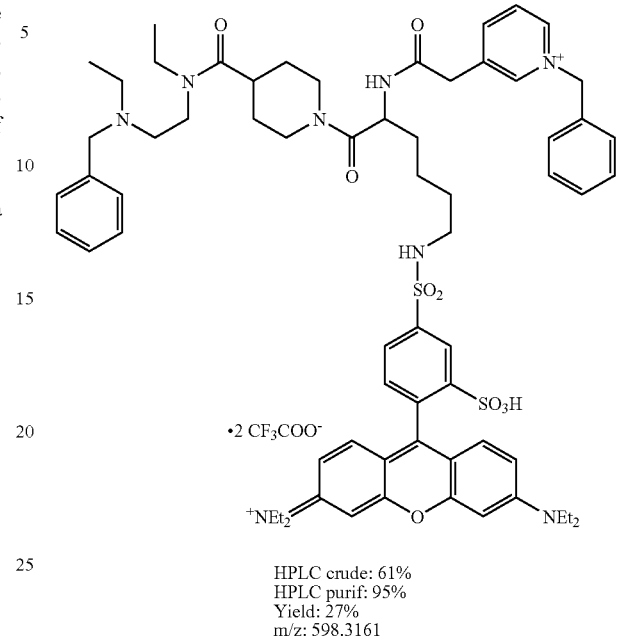

6. Incorporation of the Spacer Arm $R_5$

The interaction of the fluorophore and the fluorescent group GFP of the receptor is proportional to the distance between these two groups and optimal when the distance is comprised between 10 and 100 Å (Vollmer, J-Y.; Alix, P.; Chollet, A.; Takeda, K.; Galzi, J-L. (1999) *J. Biol. Chem.*, 274, 37915-37922; Förster (1951) in "Fluoreszenz Organischer Verbindung" Vandenhoek and Rupprecht, Göttingen; Wu; Brand (1994) *Anal Biochem*, 2181, 1-13). It therefore appears important to have a link of a different length between the fluorophore and the pharmacophore, in order to increase the chances of being located in the right distance range promoting the interaction and the FRET.

Two chain elongation techniques starting with the lysine primary amine ε have been envisaged. Each of the 2 techniques involves 2 stages: i.e. the incorporation of a Boc-protected amino acid of variable length of undecanoic or caprylic type (10 or 7 methylene units) then deprotection of the Boc or the formation of urea using p-nitrophenylchloroformate then a symmetrical diamine (Diagram 11) (Buchman, B. O.; Mohan, R. (1996) *Tetrahedron Lett.*, 37, 4439-4442; Wang, F.; Haushe, J. R. (1997) *Tetrahedron Lett.*, 38, 6529-6532).

The second method was used due to the commercial availability of the two reagents. Three diamines were tested: 1,4-diaminobutane 23a, 1,12-dodecanediamine 23b and 4,9-dioxa-1,14-dodecanediamine 23c.

The elongation is carried out using an excess (10 equivalents) of p-nitrophenylchloroformate and DIEA [0.1 M] in a THF/DCM mixture 1:1 for 2 hours at ambient temperature leading to the carbamates 24. After washing, avoiding use of methanol in order not to displace the p-nitrophenol group, the latter is displaced by the diamine 23. A high concentration of diamine is used (20 equivalents [0.2 M]) in DCM for 15 hours at ambient temperature in order to avoid any crosslinking over 2 different sites of the resin (Diagram 11).

Diagram 11

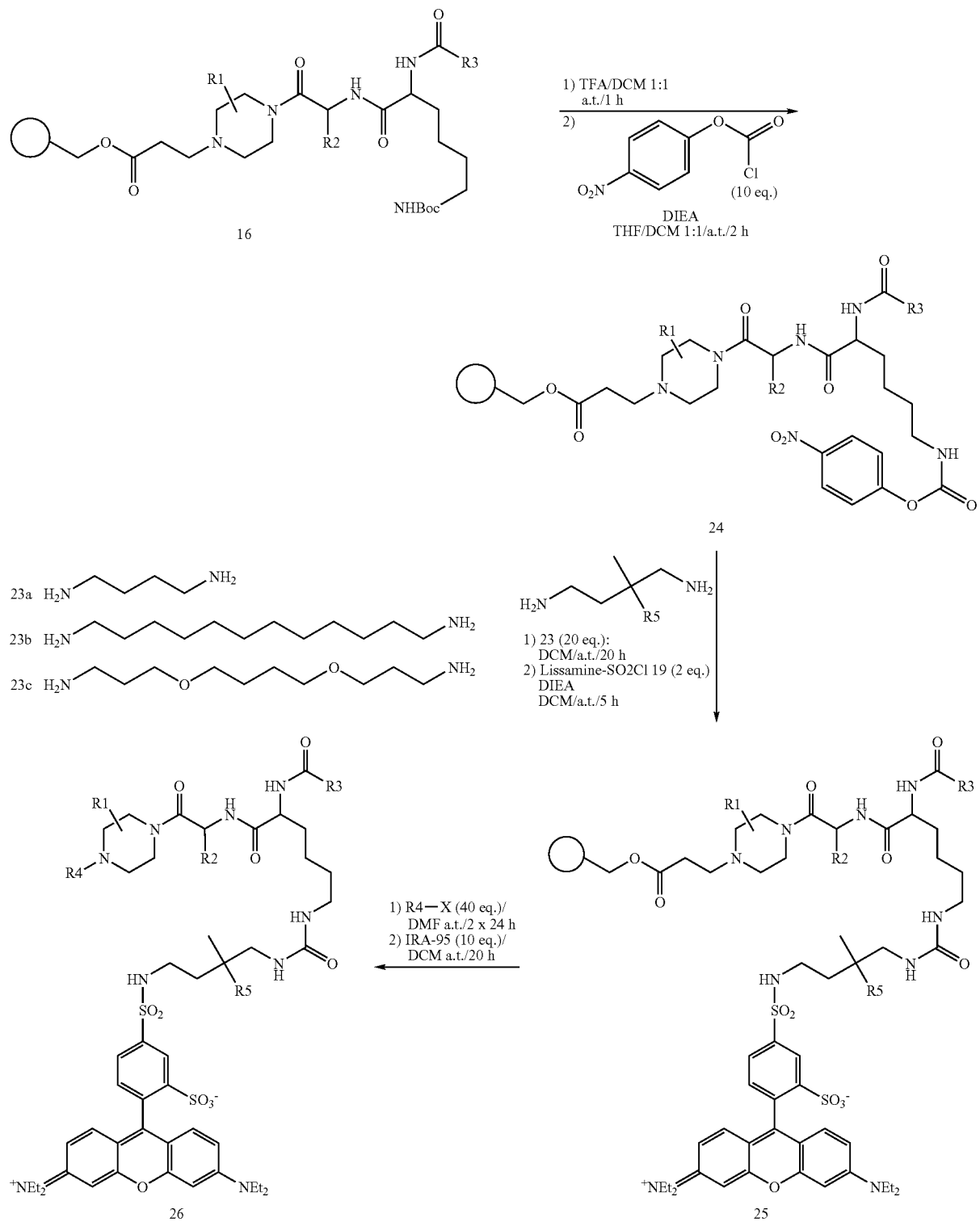

The protocol described above therefore allows the synthesis of fluorescent molecules (22 and 26) of bis-cation type from REM resin 2. Five groups ($R_1$ to $R_5$) allow the introduction of diversity at the level of the pharmacophore ($R_1$ to $R_4$) and the spacer arm ($R_5$) between the pharmacophore and the fluorophore. The preferred fluorophore is Lissamine 19f in the form of sulphonyl chloride.

II—Experimental Part

1—Equipment

The Lissamine Rhodamine B sulphonyl chloride is obtained from Acros (ref. 41323-0050). The hydroxymethyl polystyrene resin (100-200 mesh 1% DVB charge 0.6-1.6 mmol.g$^{-1}$) is obtained from Novabiochem (ref. 0164-0110). Fmoc-Lys(Boc)-OH is obtained from Advanced Chem Tech (ref. FK2390). The ion exchange resin IRA 95 (4.7 meq/g) is obtained from Sigma (ref. A8085). The washing solvents for the synthesis of the combinatorial libraries are technical dichloromethane (DCM) (chemicals store), dimethylformamide (DMF) (Riedel de Haën ref. 15440) and methanol (MeOH) (Prolabo ref. 208522.327).

Parallel synthesis on solid phase on 0.01 to 0.1 mmol at ambient temperature is carried out in polypropylene syringes equipped with a polyethylene filter obtained from Supelco (ref. 57023; 57024; 57026). These syringes are stoppered using rubber septa obtained from Aldrich (ref. Z16,725-8; Z10,073-0) or Prolabo (ref. 50627.152). Filtration is carried out by means of the "Visiprep solid phase extraction vacuum manifold" (12 positions) obtained from Supelco (ref. 57030-u). The syringes are stirred by a rotary shaker. The high-temperature reactions are carried out in Supelco transparent glass flasks (15 ml) stoppered with a polypropylene stopper and equipped with a PTFE/silicon septum (ref. 27211). The flasks are positioned on a 12-position aluminium heating block using low-speed magnetic stirring with a cylinder-shaped rod obtained from Prolabo (ref. 08553.082). Parallel synthesis on solid phase on more than 0.1 mmol at ambient temperature is carried out in 20, 50 or 80 ml "Peptide Vessels" equipped with a frit of coarse porosity or in 25 ml or 50 ml transparent glass Duran flasks from Prolabo (ref. 09926.021 and 09926.043 respectively). Stirring is carried out by a rotary shaker. The high-temperature reactions are carried out in standard single-necked glass flasks with mechanical stirring (so as not to damage the resin) or magnetic stirring at minimal speed. The parallel synthesis of combinatorial libraries is carried out using a FlexChem device from Robbins Scientific typically on 0.01 mmol. The reactions are carried out in "FlexChem polypropylene Reactor Blocks" (96-wells, 2.4 ml/well, average porosity 50-90 micron, ref. 1052-00-5). These "FlexChem polypropylene Reactor Blocks" are inserted between two metal caps (ref. 1052-01-0 and 1052-02-0) and held together by a clamping collar (ref 1052-06-0). Tightness is ensured by means of the "rubber gasket" (for use with DMF) (ref. 1052-03-1) or "Viton gasket" (for use with DCM) (ref. 1052-03-2) rubber septas. Stirring the "FlexChem polypropylene Reactor Blocks" is carried out at ambient temperature or high temperature by means of an oven with rotary stirring (ref. 1052-20-2). The Stock solutions are prepared in 25 ml or 50 ml transparent glass Duran flasks from Prolabo (ref. 09926.021 and 09926.043 respectively), as well as transparent glass VWR flasks from Prolabo (ref. 50637.908). The distribution of the reagents (50 to 1200 μl) from the stock solutions is carried out by means of electronic pipettes from Biohit (8 channels ref. 710800, 1 channel ref. 710040) with Biohit tips (50 to 1200 μl) (ref. 780046). The washing and the distribution of the solvents is carried out using an Eppendorf Multipette 4780 pipette equipped with 50 ml Combitips Plus from Prolabo (ref. 01.301.611) and with a Statmatic polypropylene 8-channel dispenser from Polylabo (ref. 66339). It is preferable to pour the reagents and the solvents into narrow-bottomed 60-ml reservoirs from Prolabo (ref. 08553.082). After cleavage, the molecules are recovered in 96-well polypropylene plates with a conical bottom and containing 2.2 ml per well, produced by AB of Polylabo (ref. 35379). Evaporation is carried out using a Genevac DD4 evaporator. Storage of the final products is carried out in the previously mentioned 96-well AB plates—equipped with an AB silicon cover from Polylabo (ref. 35858).

The melting points are determined on a Mettler FP62 device and are not corrected. The electronic ionization mass spectra (ESI-TOF) are obtained on a Mariner spectrometer (Perceptive Biosystems). The NMR $^1$H and $^{13}$C spectra are recorded on a Bruker 200 or 300 MHz spectrometer in solutions of $CDCL_3$, DMSO-d6 or MeOD. Reversed-phase analytical HPLC (RP-HPLC) is carried out on a Dionex Vydac 218TP C18 column (4.6×250 mm, 300 Å, 10μ). The elution eluents are such that gradient A: $T_{0\ min}$ 2% $H_2O$ (0.1% TFA), $T_{30\ min}$ 100% $CH_3CN$, $T_{35\ min}$ 100% $CH_3CN$ at 0.5 ml/min. The reversed-phase semi-preparative HPLC is carried out on a Dionex Vydac 218TP C18 column (22×250 mm, 300 Å, 10-15μ). The elution eluents are such that gradient B: $T_{0\ min}$ 2% $H_2O$ (0.1% TFA), $T_{5\ min}$ 35% $CH_3CN$, $T_{30\ min}$ 100% $CH_3CN$ $T_{35\ min}$ 100% $CH_3CN$ at 10 ml/min or gradient C: $T_{0\ min}$ 35% $H_2O$ (0.1% TFA), $T_{25\ min}$ 100% $CH_3CN$, $T_{30\ min}$ 100% $CH_3CN$ at 10 ml/min.

2—Preparation of the Reaction Units

1-Benzyl-4-tertbutyloxycarbonylaminopiperidine 5

In a 250 ml flask equipped with a magnetic stirrer and a dropping funnel, monohydrated 4-amino-1-benzylpiperidine dihydrochloride (16.6 g; 63 mmol) is solubilized in a solution constituted by 30 ml of aqueous KOH. (7.8 g; 139 mmol) and 60 ml of sec-butanol. A solution of di-tert-butyldicarbonate (16.5 g: 75.6 mmol) in 60 ml of sec-butanol is added slowly at ambient temperature. The mixture is then stirred at this temperature for 16 hours. After evaporation of the solvents, the residue is taken up in 200 ml of water and 200 ml of DCM. The mixture is decanted then the aqueous phase is extracted with 2×200 ml of DCM. The organic phases are washed with a saturated solution of NaCl then combined, dried ($MgSO_4$) and evaporated in order to produce 20 g of a crude product. After purification by chromatography on silica (ethyl acetate/hexane 1:1 $R_f$=0.45); 15.9 g (Yield=87%) of product are recovered in the form of white crystals.

Mass ($C_{17}H_{26}N_2O_2$=290.41; (ESI-TOF) monoisotopic m/z, calculated for $[M+H]^+$: 291.2072 g/mol, observed: 291.2110)

MP: 121° C.

$^1$H NMR (EGFMH602/41, 200 MHz, $CDCl_3$) 7.31 (m, 5H, $H_{aryl}$); 4.43 (bs, 1H, NH); 3.49 (s, 3H, $H_{benzyl}$ & $H_4$); 2.80 (d, 2H, J=12 Hz, $H_{2,6}$); 2.09 (t, 2H, J=12 Hz, $H_{3,5}$), 1.91 (d, 2H, J=12 Hz, $H_{2,6}$); 1.50 (m, 2H, $H_{3,5}$); 1.45 (s, 9H, tBu)

4-tert-Butyloxycarbonylaminopiperidine 3e

A solution of 1-benzyl-4-tertbutyloxycarbonylaminopiperidine 5 (7.95 g; 27.4 mmol) in 120 ml of MeOH is poured into a hydrogenation reactor. 10% Pd/c-based catalyst is added (1.46 g; 1.38 mmol) and the mixture is subjected to a hydrogen pressure of 3.5 bars (50 psi) for 24 hours in a Parr type shaker. After filtration on celite and washing with methanol, the medium is concentrated in order to produce 4.98 g (Yield=91%) of product in the form of white crystals.

Mass ($C_{10}H_{20}N_2O_2$=200.29; (ESI-TOF) monoisotopic m/z, calculated for $[M+H]^+$: 201.1603 g/mol; observed: 201.1698)

MP: 157° C.

¹H NMR (300 MHz, CDCl₃) 4.52 (bs, 1H, NH); 3.51 (m, 1H, H₄); 3.06 (d, 2H, J=12 Hz, H₂.₆); 2.65 (t, 2H, J=12 Hz, H₃.₅); 1.95 (bs, 1H, NH); 1.92 (d, 2H, J=12 Hz, H₂.₆); 1.43 (s, 9H, tBu); 1.27 (m, 2H, H₃.₅)

1-benzyl-4-carboxamidopiperidine 6

In a 1-l three-necked flask equipped with a condenser, a magnetic stirrer and a thermometer, isonipecotamide (12.5 g; 97.6 mmol) is added to 400 ml of hot acetonitrile. After dissolution of the reagent, sodium bicarbonate (14.7 g; 175 mmol) and benzyl bromide (12.8 ml; 107 mmol) are added. The mixture is stirred under reflux for 24 hours. The mixture is then hot-filtered in order to remove the sodium salts and these salts are washed with 50 ml of acetonitrile. After evaporation of the solvents, the residue is recrystallized from 600 ml of an ethyl acetate/hexane mixture 3:1 in order to produce 5.5 g of initial reagent and 8.69 g (Yield=41%) of product in the form of white crystals.

Mass ($C_{13}H_{18}N_2O$=218.31; (ESI-TOF) monoisotopic m/z, calculated for $[M+H]^+$: 219.1497 g/mol; observed: 219.1694)

MP: 156° C. (lit. 161° C.)

¹H NMR (200 MHz, CDCl₃) 7.31 (m, 5H, H$_{aryl}$); 5.56 (bs, 2H, NH); 3.50 (s, 2H, H$_{benzyl}$); 2.93 (d, 2H, J=12 Hz, H₂.₆); 2.01-1.76 (m, 7H)

4-aminomethyl-1-benzylpiperidine 7

In a 500 ml two-necked flask equipped with a condenser, a magnetic stirrer and placed under argon flushing, 1-benzyl-4-carboxamidopiperidine 6 (8.9 g; 40.8 mmol) is added by small portions to a suspension of LiAlH₄ (2.33 g; 61.5 mmol) in 140 ml of dry ether. The mixture is then taken to reflux under argon for 24 hours. The medium is left to cool down again to ambient temperature then poured carefully over 300 ml of a water/ice mixture. After filtration, 200 ml of ether are added then the mixture is decanted. The aqueous phase is extracted with 2×200 ml of ether. After evaporation of the solvents, 5.51 g of product (Yield=66%) is obtained in the form of a colourless oil.

Mass ($C_{13}H_{20}N_2$=204.33; (ESI-TOF) monoisotopic m/z, calculated for $[M+H]^+$: 205.1705 g/mol, observed: 205.1876)

MP: 88° C.

¹H NMR (200 MHz, CDCl₃) 7.33 (m, 5H, Haryl); 3.52 (s, 2H, Hbenzyl); 2.93 (d, 2H, J=12 Hz, H₂.₆); 2.60 (d, 2H, J=6 Hz, CH₂NH₂); 1.98 (t, 2H, J=12 Hz, H₃.₅); 1.71 (d, 2H, J=9 Hz, H₂.₆); 1.43 (bs, 2H, NH); 1.29 (m, 3H, H₃.₅ & H₄)

1-benzyl-4-tertbutyloxycarbonylaminomethylpiperidine 8

In a 100 ml flask equipped with a magnetic stirrer and a dropping funnel, 4-aminomethyl-1-benzylpiperidine 7 (3.98 g; 19.5 mmol) is dissolved in a mixture constituted by 10 ml of aqueous KOH (1.28 g; 22.9 mmol) and 20 ml of sec-butanol. A solution of di-tert-butyldicarbonate (5.45 g; 25 mmol) in 20 ml of sec-butanol is added slowly at ambient temperature. The mixture is then stirred at this temperature for 16 hours. After evaporation of the solvents, the residue is taken up in 50 ml of water and 50 ml of DCM. The mixture is decanted then the aqueous phase is extracted with 2×50 ml of DCM. The organic phases are washed with a saturated solution of NaCl then combined, dried (MgSO₄) and evaporated in order to produce the crude product. After purification by chromatography on silica (ethyl acetate/hexane 1:1 R$_f$=0.45), 4.79 g (Yield=81%) of product is recovered in the form of white crystals.

Mass ($C_{18}H_{28}N_2O_2$=304.45; (ESI-TOF) monoisotopic m/z, calculated for $[M+H]^+$: 305.2229 g/mol, observed: 305.2354)

MP: 83° C.

¹H NMR (300 MHz, CDCl₃) 7.33 (m, 5H, Haryl); 4.61 (bs, 1H, NH); 3.49 (s, 2H, Hbenzyl); 3.02 (t, 2H, J=6 Hz, CH₂NH); 2.89 (d, 2H, J=12 Hz, H₂.₆); 1.94 (td, 2H, J=12 Hz, J=2.5 Hz, H₃.₅); 1.65 (d, 2H, J=12 Hz, H₂.₆); 1.44 (s, 10H, tBu & H₄); 1.29 (td, 2H, J=12 Hz, J=3.5 Hz, H₃.₅)

4-tert-butyloxycarbonylaminomethylpiperidine 3f

A solution of 1-benzyl-4-tertbutyloxycarbonylaminomethylpiperidine 8 (4.79 g; 15.7 mmol) in 120 ml of MeOH is poured into a hydrogenation reactor. The 10% Pd/C-based catalyst is added (0.872 g; 0.82 mmol) and the mixture is subjected to a hydrogen pressure of 3.5 bars (50 psi) for 24 hours in a Parr type shaker. After filtration on celite and washing with methanol, the medium is concentrated in order to produce 3.36 g (Yield=100%) of product in the form of white crystals.

Mass ($C_{11}H_{22}N_2O_2$=214.32; (ESI-TOF) monoisotopic m/z, calculated for $[M+H]^+$: 215.1759 g/mol; observed: 215.1868)

MP: 101° C.

¹H NMR (200 MHz, CDCl₃) 4.68 (bs, 1H, NH); 3.07 (d, 2H, J=12 Hz, H₂.₆); 2.98 (t, 2H, J=6 Hz, CH₂NH); 2.57 (td, 2H, J=12 Hz, J=2.5 Hz, H₃.₅); 2.49 (bs, 1H, NH); 1.66 (d, 2H, J=12 Hz, H₂.₆); 1.43 (s, 10H, tBu & H₄); 1.14 (td, 2H, J=12 Hz, J=4 Hz, H₃.₅)

General Protocol for the Formation of Boc-Protected Amino Acids 9:

In a 100 ml flask of equipped with a magnetic stirrer and a dropping funnel, the amino acid (32 mmol) is solubilized in a solution constituted by 10 ml of aqueous KOH (1.88 g; 33.6 mmol) and 20 ml of sec-butanol. A solution of di-tert-butyl-dicarbonate (7.67 g; 35.2 mmol) in 20 ml of sec-butanol is added slowly at ambient temperature. The mixture is then stirred at this temperature for 16 hours. After the addition of 200 ml of water, the mixture is extracted with 3×75 ml of hexane. The aqueous phase is cooled down with 100 g of ice then acidified to pH=2 with 1N KHSO₄. After extraction with 3×100 ml of ethyl acetate, the organic phases are dried (MgSO₄) and concentrated in order to produce a generally pure product in the form of white crystals. Recrystallization from an ethyl acetate/ether mixture is carried out in certain cases.

4-N-tert-butyloxycarbonylaminomethylbenzoic acid 9a (Smith, J., Liras, J. L.; Schneider, S. E.; Anslyn, E. V. (1996) *J. Org. Chem.*, 61, 8811-08818)

Yield=80%

Mass ($C_{13}H_{17}NO_4$=251.29; (ESI-TOF) monoisotopic m/z, calculated for $[M+Na]^+$: 274.1055 g/mol; observed: 274.1181)

MP: 164° C. (Lit: 158° C.)

¹H NMR (200 MHz, MeOD) 8.01 (d, 2H, J=8 Hz, H₂.₆); 7.40 (d, 2H, J=8 Hz, H₃.₅); 4.33 (s, 2H, CH₂NH); 1.49 (s, 9H)

4-N-tert-butyloxycarbonylaminomethylcyclohexanoic acid 9b

Yield=82%

Mass ($C_{13}H_{23}NO_4$=257.34; (ESI-TOF) monoisotopic m/z calculated for $[M+Na]^+$: 280.1525 g/mol; observed: 280.1669)

MP: 133° C.

¹H NMR (200 MHz, CDCl₃) 4.65 (bs, 1H, NH); 2.99 (m, 2H, CH₂NH); 2.29 (t, 1H, J=12 Hz, H₁); 2.07 (d, 2H, J=12 Hz,

H$_{2,6}$); 1.86 (d, 2H, J=12 Hz, H$_{2,6}$); 1.47 (m, 13H, tBu, 2H$_{3,5}$ & H$_4$); 1.02 (q, 2H, J=12 Hz, H$_{3,5}$)

8-N-tert-butyloxycarbonylaminocaprylic acid 9c (Huang, W.; Kalivretenos, A. G. (1995) *Tetrahedron Lett.*, 36, 9113-9116)
Yield=70%
Mass (C$_{13}$H$_{25}$NO$_4$=259.36; (ESI-TOF) monoisotopic m/z, calculated for [M+H]$^+$: 260.1862 g/mol, observed: 260.2164)
MP: 162° C.
$^1$H NMR (200 MHz, CDCl$_3$) 4.53 (bs, 1H, NH); 3.10 (m, 2H, CH$_2$NH); 2.34 (t, 2H, J=8 Hz); 1.63-1.33 (m, 10H); 1.45 (s, 9H, tBu)

N-tert-butyloxycarbonylpipecolinic acid 9d (Johnson, R. J.; Rajakumar, G.; Yu, K.-L.; Mishra, R. K. (1986) *J. Med. Chem.*, 29, 2104-2107)
Yield=65%
Mass (C$_{11}$H$_{19}$NO$_4$=229.29; (ESI-TOF) monoisotopic m/z, calculated for [M+H]$^+$: 230.1392 g/mol, observed: 230.1532)
MP: 129° C.
$^1$H NMR (300 MHz, CDCl$_3$) 9.42 (bs, 1H, OH); 4.94-4.78 (bm, 1H, H$_2$); 3.97 (m, 1H, H$_6$); 2.97 (m, 1H, H$_6$); 2.24 (d, 1H, J=16 Hz); 1.69 (m, 3H); 1.47 (s, 9H tBu); 1.43-1.33 (m, 2H)

N-tert-butyloxycarbonyl-tetrahydroisoquinoline-3-carboxylic acid 9e

Yield=66%
Mass (C$_{15}$H$_{19}$NO$_4$=277.33; (ESI-TOF) monoisotopic m/z, calculated for [M+H (Cl$^{35}$)]$^+$: 278.1392 g/mol, observed: 278.1529)
MP: 123° C.
$^1$H NMR (200 MHz, CDCl$_3$) 7.17 (m, 4H, H$_{aryl}$); 6.50 (bs, 1H, OH); 5.10 (bs, 1H, NH); 4.70 (d, 2H, J=16 Hz, CH$_2$NH); 4.48 (d, 1H, J=16 Hz, CHα); 3.17 (m, 2H, CH$_2$β); 1.51-1.41 (m, 9H tBu)

N-tert-butyloxycarbonyl-4-chlorophenylalanine 9h (Millington, C. R; Quarrell, R.; Lowe, G. (1998) *Tetrahedron Lett.*, 39, 7201-7204)
Yield=58%
Mass (C$_{14}$H$_{18}$NO$_4$Cl=299.77; (ESI-TOF) monoisotopic m/z, calculated for [M+H (Cl$^{35}$)]$^+$: 300.1002 g/mol, observed: 300.1529)
MP: 147° C.
$^1$H NMR (300 MHz, CDCl$_3$) 9.81 (bs, 1H, OH); 7.28 (d, 2H, J=8 Hz, H$_{2,6}$); 7.13 (d, 2H, J=8 Hz, H$_{2,6}$); 5.00 (d, 1H, J=7 Hz, NH); 4.62-4.37 (m, 1H, CHα); 3.20-3.02 (m, 2H, CH$_2$N); 1.43-1.35 (m, 9H tBu)

N-tert-butyloxycarbonylisonipecotinic acid 9i

Yield=88%
Mass (C$_{11}$H$_{19}$NO$_4$=229.29; (ESI-TOF) monoisotopic m/z, calculated for [M+H]$^+$: 230.1392 g/mol, observed: 230.1621)
MP: 149° C.
$^1$H NMR (200 MHz, CDCl$_3$) 9.58 (bs, 1H, OH); 4.01 (d, 2H, J=12 Hz, H$_{2,6}$); 2.83 (dt, 2H, J=12 Hz, J=3 Hz, H$_{2,6}$); 2.48 (m, 1H, H$_1$); 1.91 (dd, 2H, J=12 Hz, J=3 Hz, H$_{3,5}$); 1.68 (dt, 2H, J=12 Hz, J=3 Hz, H$_{3,5}$); 1.46 (s, 9H tBu)

1-N-tert-butyloxycarbonylaminocyclopentane-1-carboxylic acid 9f (Khalil, E. M.; Subasinghe, N. L.; Johnson, R. L. (1996) *Tetrahedron Lett.*, 37, 3441-3444)

A mixture of 1-aminocyclopentane-1-carboxylic (4.13 g; 32 mmol) and pentahydrated tetramethylammonium hydroxide (5.79 g; 32 mmol) is stirred at ambient temperature in 200 ml of acetonitrile. Di-tert-butyldicarbonate (10.46 g; 48 mmol) is added and the mixture is stirred for 48 hours at ambient temperature. An excess of di-tert-butyldicarbonate (3.49 g; 16 mmol) is added and the mixture is stirred for another 24 hours at ambient temperature. The solvent is evaporated off under reduced pressure. After the addition of 200 ml of water, the mixture is extracted with 3×75 ml of hexane. The aqueous phase is cooled down with 100 g of ice then acidified to pH=2 with 1N KHSO$_4$. After extraction with 3×100 ml of ethyl acetate, the organic phases are dried (MgSO$_4$) and concentrated in order to produce 4.35 g of product (Yield=59%) in the form of white crystals.

Mass (C$_{11}$H$_{19}$NO$_4$=229.29; (ESI-TOF) monoisotopic m/z, observed for [M+H]$^+$: 230.1532 g/mol)
MP: 131° C. (Lit.: 133° C.)
$^1$H NMR (200 MHz, CDCl$_3$) 8.22 (bs, 1H, OH); 5.01 (bs, 1H, NH); 2.38-2.24 (m, 2H); 2.00-1.79 (m, 6H); 1.48 (s, 9H, tBu)

4-phenyl-N-tert-butyloxycarbonylpiperidine-4-carboxylic acid 9g (Bukholder, T. P.; Kudlacz, E. M.; Maynard, G. D.; Liu, X.-G.; Le, T-B.; et al. (1997) *Bioorg. Med. Chem. Lett.*, 7, 2531)

In a 100 ml flask equipped with a magnetic stirrer and a dropping funnel, the tosylate salt of 4-phenyl-4-piperidine carboxylic acid (12.06 g; 32 mmol) is solubilized in a solution constituted by 20 ml of aqueous KOH (3.76 g; 67.1 mmol) and 40 ml of sec-butanol. A solution of di-tert-butyldicarbonate (7.67 g; 35.2 mmol) in 20 ml of sec-butanol is added slowly at ambient temperature. The mixture is then stirred at this temperature for 16 hours. After the addition of 200 ml of water, the mixture is extracted with 3×75 ml of hexane. The aqueous phase is cooled down with 100 g of ice then acidified to pH=2 with 1N KHSO$_4$. After extraction with 3×100 ml of ethyl acetate, the organic phases are dried (MgSO$_4$) and concentrated in order to produce 6.84 g of a crude product which is recrystallized from ethyl acetate in order to produce 4.32 g of product (Yield=44%) in the form of white crystals.

Mass (C$_{17}$H$_{23}$NO$_4$=305.39; (ESI-TOF) monoisotopic m/z, calculated for [M+H]$^+$: 306.1705 g/mol, observed: 306.1970)
MP: 187° C.
$^1$H NMR (300 MHz, CDCl$_3$) 7.43-7.28 (m, 5H, H$_{aryl}$); 3.93 (d, 2H, J=12 Hz, H$_{2,6}$); 3.10 (t, 2H, J=12 Hz, H$_{2,6}$); 2.50 (d, 2H, J=12 Hz, H$_{3,5}$); 1.88 (t, 2H, J=12 Hz, H$_{3,5}$); 1.45 (s, 9H tBu)

N-benzylproline 18a (cf Diagram 6)

In a 100 ml three-necked flask equipped with a magnetic stirrer, a thermometer, a dropping funnel and a condenser, a solution of proline (5.76 g; 50 mmol) and KOH (8.47 g; 151 mmol) in 35 ml of isopropanol is prepared by heating the mixture to 50° C. The medium becomes homogeneous after 30 minutes then benzyl bromide (7.2 ml; 60 mmol) is added over 30 minutes at 50° C. The mixture is heated for 5 hours at this temperature. The mixture is then left to cool down to ambient temperature then the pH is adjusted to 5-6 with concentrated HCl. After the addition of 15 ml of CHCl$_3$, the mixture is stirred for 16 hours at ambient temperature. The mixture is then filtered and the precipitate is washed with 2×20 ml of CHCl$_3$. The filtrate is concentrated under reduced pressure in order to produce a solid which is washed with acetone. After drying under vacuum using a vane pump, 8.80 g of product is obtained (Yield=86%) in the form of white crystals.

Mass ($C_{12}H_{15}NO_2$=205.27; (ESI-TOF) monoisotopic m/z, calculated for $[M+H]^+$: 206.1181 g/mol, observed: 206.1423)

MP: 170° C. (lit. 174° C.)

$^1$H NMR (300 MHz, DMSO-d6) 8.71 (bs, 1H, OH); 7.41-7.34 (m, 5H, $H_{aryl}$); 4.18 (d, 1H, J=12 Hz); 3.90 (d, 1H, J=12 Hz); 3.52 (m, 1H); 3.16 (m, 1H); 2.76 (q, 1H J=9 Hz); 2.15 (q, 1H J=9 Hz); 1.90-1.71 (m, 3H)

N-diphenylmethylproline 18b

In a 100 ml three-necked flask equipped with a magnetic stirrer, a thermometer, a dropping funnel and a condenser, a solution of proline (5.76 g; 50 mmol) and KOH (8.47 g; 151 mmol) in 35 ml of isopropanol is prepared by heating the mixture to 50° C. The medium becomes homogeneous after 30 minutes then chlorodiphenylmethane (10.7 ml; 60 mmol) is added over 30 minutes at 50° C. The mixture is heated for 5 hours at this temperature. The mixture is then left to cool down to ambient temperature. After the addition of 100 ml of water, the pH is adjusted to 10 and 9.80 g of chlorodiphenylmethane (80%) is recovered after extraction with $CHCl_3$. The pH is adjusted to 5-6 with concentrated HCl and the mixture is extracted once again with chloroform in order to produce 2.15 g of product (Yield=15%) in the form of brown-coloured crystals.

Mass ($C_{18}H_{19}NO_2$=281.36; (ESI-TOF) monoisotopic m/z, calculated for $[M+H]^+$: 282.14939 g/mol, observed: 282.1784)

MP: 167° C.

$^1$H NMR (300 MHz, $CDCl_3$) 8.85 (bs, 1H, OH); 7.47-7.30 (m, 10H, $H_{aryl}$); 4.82 (s, 1H, $CHPh_2$); 4.18 (d, 1H, J=12 Hz); 3.68 (dd, 1H, J=9 Hz, J=3.5 Hz); 3.32 (m, 1H); 2.69 (q, 1H J=9 Hz); 2.21 (m, 2H); 1.89 (m, 2H)

N-diphenylmethylsarcosine 18c

In a 250 ml three-necked flask equipped with a magnetic stirrer, a thermometer, a dropping funnel and a condenser, a mixture of sarcosine (4.45 g; 50 mmol) and KOH (8.47 g; 151 mmol) in 70 ml of isopropanol is prepared by heating the mixture to 50° C. The medium remains cloudy after 30 minutes then chlorodiphenylmethane (10.7 ml; 60 mmol) is added over 30 minutes at 50° C. The mixture is heated for 5 hours at this temperature. The mixture is then left to cool down to ambient temperature. After the addition of 100 ml of water, the pH is adjusted to 10 and the chlorodiphenylmethane which has not reacted is recovered after extraction with $CHCl_3$. The pH is adjusted to 5-6 with concentrated HCl and the mixture is extracted once again with chloroform in order to produce 2.23 g of product (Yield=18%) in the form of colourless gum.

Mass ($C_{16}H_{17}NO_2$=255.33; (ESI-TOF) monoisotopic m/z, calculated for $[M+H]^+$: 256.1337 g/mol, observed: 256.1545)

$^1$H NMR (200 MHz, $CDCl_3$) 7.43-7.30 (m, 11H, $H_{aryl}$ & OH); 4.89 (s, 1H, $CHPh_2$); 3.34 (s, 2H, Hα); 2.46 (s, 3H, $CH_3N$)

Arecaidine hydrochloride 18d (Martin, A. R.; Paradkar, V. M.; Peng, G. W.; Speth, R. C.; Yamamura, H. I.; Horn, A. S. (1980) *J. Med. Chem.*, 23, 865-873)

In a 250 ml flask equipped with a magnetic stirrer and a condenser, arecoline hydrochloride (4 g; 20.9 mmol) is added to a solution of 50 ml of 95% ethanol and 60 ml of concentrated HCl. The mixture is heated at 100° C. for 12 hours then at reflux for 6 hours. The solvents are evaporated off under reduced pressure leaving a solid residue. The residue is recrystallized from a 95% ethanol/ether mixture in order to produce 1.69 g of product (Yield=46%) in the form of white crystals.

Mass ($C_7H_{11}NO_2$+HCl=177.63; (ESI-TOF) monoisotopic m/z, calculated for $[M+H]^+$: 142.0867 g/mol, observed: 142.0817)

MP: 247° C. (lit. 261° C.)

$^1$H NMR (300 MHz, MeOD) 7.15 (s, 11H); 4.14 (bm, 1H); 3.81 (bm, 1H); 3.57 (bm, 1H); 3.25 (bm, 1H); 3.02 (s, 3H); 2.70 (bs, 2H)

3—Multi-Stage Synthesis

REM Resin 2

Hydroxymethylpolystyrene resin 1 (10.3 g; 12.8 mmol) [Novabiochem 1.24 mmol/g, 100-200 Mesh] is placed in a 250 ml flask. The resin is expanded with 100 ml of dichloromethane then diisopropylethylamine (16.5 g; 128 mmol) is added. The suspension is stirred with a magnetic stirrer adjusted to the lowest speed then acryloyl chloride (11.6 g; 128 mmol) is added in 4 portions. The stirring is continued at ambient temperature for 24 hours then the resin is filtered and washed with DMF and dichloromethane. The reaction is repeated once before the filtration. The final washing is carried out with 2 sequences of DMF, dichloromethane and MeOH, finishing with $Et_2O$. The resin is dried under vacuum using a vane pump for 24 hours in order to produce 11.2 g of resin (theoretical load 1.16 mmol.$g^{-1}$). The formation of the acrylate is confirmed by IR analysis (vibration of the carbonyl at 1727 $cm^{-1}$ and of the alkene at 1403 $cm^{-1}$).

General Protocol for Michael Addition on REM Resin

The REM resin 2 (3.5 g; 4.74 mmol; 1.35 mmol.$g^{-1}$ theoretical load) is expanded in 10 ml of DMF, then a solution of diamine 3 (47.4 mmol) in DMF (40 ml) is added to the suspension. After stirring on the rotary shaker for 24 hours at ambient temperature, the resin is filtered and washed with DMF and dichloromethane. The reaction is repeated once. The final washing is carried out with 2 sequences of DMF, dichloromethane and MeOH, finishing with $Et_2O$. The resin is dried under vacuum using a vane pump for 16 hours. The determination of the load is obtained on an aliquot of 25 mg of resin by the Fmoc test method (after coupling with 5 equivalents of Fmoc-Phe-OH/DIC/HOBt for 6 hours at ambient temperature, followed by a deprotection using piperidine; the absorbance of the fulvene-piperidine adduct generated in solution is measured at 301 nm, $\epsilon$=7800 mol.$L^{-1}$.$m^{-1}$). For reasons of solubility, the protocol is modified for 4-tert-butyloxycarbonylaminopiperidine 3e. The reaction is carried out in a flask equipped with a magnetic stirrer and a hot solution (80° C.) of Boc-monoprotected amine in DMF is added to the resin. The Michael addition is continued for 16 hours at 80° C. and is not repeated. The compounds which are Boc-monoprotected in regioselective manner are used in the case of the asymmetrical diamines. A stage of Boc-deprotection is therefore necessary after the Michael addition. The resin (2 g) is expanded in DCM (20 ml) then a solution of TFA/DCM 3:1 (40 ml) is added. After reaction for 1 hour at ambient temperature, the resin is filtered, then washed with 3 sequences of DMF, DCM, 10% DIEA in DCM, MeOH, finishing with $Et_2O$. The resin is then dried under vacuum using a vane pump for 16 hours.

General Protocol for the Coupling of Amino Acid to a Resin Functionalized by an Amino Group A solution of preactivated acid is prepared by mixing carboxylic acid (13.5 mmol) and HOBt (13.5 mmol) in DMF (30 ml) for 15 minutes at ambient temperature. A solution of DIC (13.5 mmol) in DMF (10 ml) is then added and the mixture is again stirred for 15 minutes at ambient temperature. During this time, the resin (3.75 g; 4.5 mmol; 1.20 mmol.g$^{-1}$ theoretical load) is expanded in DMF (20 ml) for 30 minutes without stirring. The preactivated acid solution (13.5 mmol) is added to the resin and the mixture is stirred on a rotary shaker for 6 hours at ambient temperature. The resin is filtered and washed using 3 sequences of DMF, dichloromethane and MeOH then Et$_2$O. The resin is then dried under vacuum using a vane pump for 16 hours.

General Protocol for the Cleavage of Esters by Transesterification

Resins of the polystyryl N,N-dialkylaminoethanoate type 10 (300 mg; 0.277 mmol; 0.93 mmol.g$^{-1}$ theoretical load) are expanded in 4 ml of THF in a 50 ml flask equipped with a magnetic stirrer and a condenser. A solution of sodium methylate (15 mg; 0.277 mmol) in 16 ml of dry MeOH is added to the suspension and the mixture is stirred at 65° C. for 20 hours. After cooling down, the resin is filtered then washed with MeOH and DCM (3×5 ml). The filtrates are collected and evaporated. The residue is taken up in DCM (30 ml) and a 5% solution of NaHCO$_3$ (30 ml). The organic phase is separated and the aqueous phase is reextracted with DCM (2×30 ml). The organic phases are combined, dried (MgSO$_4$) and evaporated to dryness in order to produce the corresponding methyl esters 11.

3-[4-(2-tert-Butoxycarbonylamino-3-phenylpropionyl)-piperazin-1-yl]-propionic acid ethyl ester 11

Yield: 95 mg of yellow gum (82%).
HPLC: 82% dionex, gradient A, Rt 24.3 min.
Mass (C$_{22}$H$_{33}$N$_3$O$_5$=419.54; (ESI-TOF) monoisotopic m/z, calculated for [M+H]$^+$: 420.2498 g/mol, observed: 420.2776)
$^1$H NMR (300 MHz, CDCl$_3$) 7.29-7.19 (m, 5H); 5.45 (brd d, J=8.3 Hz, 1H, NH); 4.81 (q, J=6.0 Hz, 1H, HαPhe); 3.62 (s, 3H, MeO); 3.52 (m, 2H, H$_{2.6}$piperazine); 3.28 (m, 1H, HβPhe); 2.98 (m, 1H, HβPhe); 2.96 (t, J=8.3 Hz, 2H, H$_{2.6}$piperazine); 2.58 (t, J=7.2 Hz, 2H, CH$_2$CH$_2$); 2.42 (t, J=6.8 Hz, 2H, CH$_2$CH$_2$); 2.36 (m, 1H, Hpiperazine); 2.23 (m, 2H, H$_{3.5}$piperazine); 1.77 (m, 1H, Hpiperazine); 1.42 (s, 9H, tBu).
$^{13}$C NMR (50 MHz, CDCl$_3$) 173.04 (Cester); 170.31 (Camide); 155.43 (Ccarbam); 136.83 (C$_1$ph); 129.97 (C$_{3.5}$ph); 128.92 (C$_{2.6}$ph); 127.35 (C$_4$ph); 80.10 (CtBu); 53.58 (C$_{MeO}$); 52.74 (C$_{3.5}$piperazine); 52.54 (C$_{3.5}$piperazine); 52.06 (N—CH$_2$CH$_2$); 51.24 (CαPhe); 45.83 (C$_{2.6}$piperazine); 42.21 (C$_{2.6}$piperazine); 40.79 (C$_{βPhe}$); 32.30 (CO—CH$_2$CH$_2$); 28.73 (CtBu).

General Protocol for REM Resin Cleavage by Quaternarization and Hofmann Elimination Tertiary amine type resin (300 mg, 279 μmol, 0.93 mmol.g$^{-1}$ theoretical load) is expanded in DMF (8 ml) and methyl iodide or benzyl bromide (11.2 mmol) is added. The mixture is stirred for 20 hours on a rotary shaker at ambient temperature. The resin is then filtered and washed with DMF, DCM and DMF. The reaction is repeated once, then after filtration, the final washing is carried out using 3 sequences of DMF, dichloromethane and MeOH then Et$_2$O. The resin is then dried under vacuum using a vane pump for 6 hours. The resin is suspended in DCM (8 ml) and the base (DIEA (2.79 mmol) or resin IRA-95 (4.7 mequ/g; 0.59 g; 2.79 mmol)) is added. The mixture is stirred for 20 hours on a rotary shaker at ambient temperature. The resin is filtered then washed with MeOH and DCM (3×5 ml). The filtrates are collected and evaporated. The residue is taken up in DCM (30 ml) and a 5% solution of NaHCO$_3$ (30 ml). The organic phase is separated and the aqueous phase is reextracted with DCM (2×30 ml). The organic phases are combined, dried (MgSO$_4$) and evaporated to dryness in order to produce the corresponding tertiary amines.

1-Benzyl-2-(4-methylpiperazin-1-yl)-2-oxo-ethyl]-carbamic acid tert-butyl ester 13a Yield: 95 mg of yellow gum (95%).
HPLC: 86% dionex, gradient A, Rt 23.0 minutes.
Mass (C$_{19}$H$_{29}$N$_3$O$_3$=347.47; (ESI-TOF) monoisotopic m/z, calculated for [M+H]$^+$: 348.2287 g/mol; observed: 348.1748)
$^1$H NMR (300 MHz, CDCl$_3$) δ 7.24-7.19 (m, 5H, Ph); 5.47 (brd d, J=8.7 Hz, 1H, NH); 4.81 (q, J=6.4 Hz, 1H, HαPhe); 3.54 (m, 2H, H$_{2.6}$piperazine); 3.31 (m, 1H, HβPhe); 2.95-3.05 (m, 3H, HβPhe & H$_{2.6}$piperazine); 2.27 (m, 1H, H$_{piperazine}$); 2.15-2.23 (m, 2H, H$_{3.5 piperazine}$); 2.17 (s, 3H, MeN); 1.74 (m, 1H, H$_{piperazine}$); 1.42 (s, 9H, tBu).
$^{13}$C NMR (50 MHz, CDCl$_3$) 170.35 (C$_{amide}$); 155.45 (C$_{carbon}$); 136.87 (C$_1$ph); 129.96 (C$_{3.5}$ph); 128.91 (C$_{2.6}$ph); 127.34 (C$_4$ph); 80.03 (C$_{βBu}$); 54.82 (C$_{3.5}$piperazine); 54.73 (C$_{3.5}$piperazine); 51.27 (CαPhe); 46.18 (C$_{MeN}$); 45.72 (C$_{2.6}$piperazine); 42.16 (C$_{2.6}$piperazine); 40.81 (C$_{βPhe}$); 28.73 (CtBu).

[1-Benzyl-2-(4-methyl-[1.4]-diazepan-1-yl)2-oxoethyl]-carbamic acid tert-butyl ester 13b Yield: 30 mg of yellow oil (40%).
HPLC: >95% dionex, gradient A, Rt 23.5 minutes.
Mass (C$_{20}$H$_{31}$N$_3$O$_3$=361.50; (ESI-TOF) monoisotopic m/z, calculated for [M+H]$^+$: 362.2443 g/mol, observed: 362.1955)
$^1$H NMR (300 MHz, CDCl$_3$) δ 7.37-7.19 (m, 5H, Ph); 5.34 (brd, 1H, NH); 4.79 (m, 1H, HαPhe); 3.64 (m, 2H, H$_{homopip}$); 3.37 (m, 1H, HβPhe); 2.96-3.15 (m, 3H, HβPhe & H$_{homopip}$); 2.18-2.72 (m, 4H, H$_{homopip}$); 2.36 (s, 3H, MeN); 1.91 (m, 2H, H$_{homopip}$); 1.87 (s, 9H, tBu).

[1-(Ethyl-[2-ethylmethylamino)-ethyl]-carbamoyl)-2-phenylethyl)-carbamic acid tert-butyl ester 13c Yield: 50 mg of yellow oil (89%).
HPLC: >95% dionex, gradient A, Rt 25.0 min.
Mass (C$_{21}$H$_{35}$N$_3$O$_3$=377.55; (ESI-TOF) monoisotopic m/z, calculated for [M+H]$^+$: 378.2756 g/mol, observed: 378.2136)
$^1$H NMR (300 MHz, CDCl$_3$) 7.23-7.19 (m, 5H, Ph); 5.30 (brd, 1H, NH); 4.72 (m, 1H, HαPhe); 3.83 (m, 1H); 3.60 (m, 1H, HβPhe); 3.34 (m, 1H, HβPhe); 2.96-3.13 (m, 3H); 2.64 (m, 3H); 2.40 (s, 3H, MeN); 1.40 (s, 9H, tBu); 1.16 (t, J=7.2 Hz, 2H); 1.01 (t, J=7.2 Hz, 4H).

[1-Benzyl-2-oxo-2-(2,4,5-trimethylpiperazin-1-yl) ethyl]-carbamic acid tert-butyl ester 13d Yield: 12 mg of yellow oil (21%)
HPLC: >95% dionex, gradient A, Rt 24.2 min.
Mass (C$_{21}$H$_{33}$N$_3$O$_3$=375.53; (ESI-TOF) monoisotopic m/z, calculated for [M+H]$^+$: 376.2599 g/mol, observed: 376.2008)

[1-(1-methylpiperidin-4-ylcarbamoyl)-2-phenyl-ethyl]-carbamic acid tert-butyl ester 13e Yield: 47 mg of white solid (80%).
HPLC: >95% dionex, gradient A, Rt 22.7 minutes.
Mass ($C_{20}H_{31}N_3O_3$=361.50; (ESI-TOF) monoisotopic m/z, calculated for [M+H]$^+$: 362.2443 g/mol, observed: 362.2758)
$^1$H NMR (200 MHz, CDCl$_3$) 7.24-7.19 (m, 5H, Ph); 5.47 (brd d, J=8.7 Hz, 1H, NH); 4.81 (q, J=6.4 Hz, 1H, HαPhe); 3.54 (m, 2H, H$_{2.6}$piperazine); 3.31 (m, 1H, HβPhe); 2.95-3.05 (m, 3H, HβPhe & H$_{2.6}$piperazine); 2.27 (m, 1H, Hpiperazine); 2.15-2.23 (m, 2H, H$_{3.5}$piperazine); 2.17 (s, 3H, MeN); 1.74 (m, 1H, Hpiperazine); 1.42 (s, 9H, tBu).
$^{13}$C NMR (75 MHz, CDCl$_3$) 170.78 ($C_{amide}$); 155.73 ($C_{carbon}$); 137.19 ($C_1$ph); 129.71 ($C_{3.5}$ph); 129.08 ($C_{2.6}$ph); 127.39 ($C_4$ph); 80.58 (CtBu); 56.50 (CαPhe); 54.51 ($C_{2.6}$); 46.36 ($C_{MeN}$); 46.13 ($C_4$); 39.27 ($C_{βPhe}$); 32.07 ($C_{3.5}$); 28.69 (CtBu).

(1-[(1-methylpiperidin-4-ylmethyl)-carbamoyl]-2-phenylethyl)-carbamic acid tert-butyl ester 13f Yield: 27 mg of white solid (34%).
HPLC: >95% dionex, gradient A, Rt 23.4 minutes.
Mass ($C_{21}H_{32}N_3O_3$=375.53; (ESI-TOF) monoisotopic m/z, calculated for [M+H]$^+$: 376.2600 g/mol, observed: 376.2112)
$^1$H NMR (200 MHz, CDCl$_3$) 7.37-7.19 (m, 5H, Ph); 5.94 (brd t, J=6.1 Hz, 1H, NH); 5.10 (brd, 1H, NH); 4.30 (q, J=7.1 Hz, 1H, HαPhe); 3.09 (m, 4H, H$_{2.6}$ & HβPhe); 2.88 (brd d, J=11.7 Hz, 1H, H$_7$); 2.32 (s, 3H, MeN); 1.97 (td, J=11.5 Hz, J=2.9 Hz, 2H, H$_{2.6}$); 1.54-1.28 (m, 14H, H$_{3,4,5}$ & tBu).

General Protocol for Boc Group Deprotection

The resin functionalized by an N-tert-butyloxycarbonyl group (3.89 g; 3.62 mmol; 0.93 mmol.g$^{-1}$ theoretical load) is expanded in 15 ml of DCM then a solution of TFA/DCM 3:1 (35 ml) is added. After deprotection for one hour at ambient temperature, the resin is filtered, and washed using 3 sequences of DMF, 10% DIEA (DCM), dichloromethane and MeOH then Et$_2$O. The resin is then dried under vacuum using a vane pump for 6 hours.

General Protocol for the Coupling of the Fmoc-Lys(Boc)-OH Derivatization Platform A solution of preactivated acid (HOBt ester) is prepared by mixing firstly N-α-Fmoc-N-ε-Boc-Lysine (5.08 g; 10.9 mmol) and HOBt (1.66 g; 10.9 mmol) in DMF (30 ml) for 15 minutes at ambient temperature. DIC (1.70 ml; 10.9 mmol) in DMF (10 ml) is then added to the mixture and the medium is stirred for 15 minutes at ambient temperature. During this time, the supported primary amine (3.62 mmol) is expanded in DMF (30 ml) for 30 minutes without stirring. The preactivated acid solution (10.9 mmol) is now added to the resin and the mixture is stirred on the rotary shaker for 6 hours at ambient temperature. The resin is then filtered and washed using 3 sequences of DMF, dichloromethane and MeOH then Et$_2$O. The resin is then dried under vacuum using a vane pump for 6 hours.

[5-[1-benzyl-2-(4-methylpiperazin-1-yl)-2-oxoethyl carbamoyl]-5-(9H-fluoren-9-ylmethoxycarbonylamino)-pentylcarbamic acid tert-butyl ester 15a Compound 15a is obtained after quaternarization using methyl iodide and Hofmann elimination in accordance with the general protocol.
Yield: 99 mg of white solid (67%).
HPLC: >95% dionex, gradient A, Rt 29.1 minute.
Mass ($C_{40}H_{51}N_5O_6$=697.91; (ESI-TOF) monoisotopic m/z, calculated for [M+H]$^+$: 698.3917 g/mol, observed: 698.4302)
$^1$H NMR (200 MHz, CDCl$_3$) 7.77-7.19 (m, 13H, Ph & Fmoc); 7.04 (brd d, J=7.3 Hz, 1H, NH); 5.55 (brd d, J=7.3 Hz, 1H, NH); 5.10 (q, J=7.3 Hz, 1H, HαLys); 4.76 (m, 1H, HαPhe); 4.39 (d, J=6.4 Hz, 2H, HFmoc); 4.21 (t, J=6.8 Hz, 1H, HFmoc); 3.54 (m, 2H, H$_{2.6}$piperazine); 3.30 (m, 1H, HβPhe); 3.10-2.94 (m, 5H, HεLys, HβPhe & H$_{2.6}$piperazine); 2.35-2.17 (m, 4H, H$_{3.5}$piperazine); 2.18 (s, 3H, MeN); 1.81 (m, 2H, HβLys); 1.48-1.42 (m, 13H, HχLys, HδLys & tBu).
$^{13}$C NMR (50 MHz, CDCl$_3$) 171.54 ($C_{amide}$); 169.66 ($C_{amide}$); 156.58 ($C_{carbam}$); 144.21 ($C_{fmoc}$); 141.71 ($C_{fmoc}$); 136.30 ($C_1$ph); 129.98 ($C_{3.5}$ph); 129.02 ($C_{2.6}$ph); 128.14 ($C_{fmoc}$); 127.52 ($C_4$ph); 125.53 ($C_{fmoc}$); 120.39 ($C_{fmoc}$); 79.60 (CtBu); 67.47 ($C_{fmoc}$); 55.18 (CαLys); 54.69 ($C_{2.6}$piperazine); 50.23 (CαPhe); 47.58 ($C_{fmoc}$); 46.18 ($C_{MeN}$); 45.81 ($C_{3.5}$piperazine); 42.34 ($C_{3.5}$piperazine); 40.10 ($C_β$Phe); 40.06 ($C_ε$Lys); 32.88 ($C_β$Lys); 29.99 ($C_δ$Lys); 28.86 (CtBu); 22.83 ($C_χ$Lys).

General Protocol for Fmoc Group Deprotection

The resin functionalized by an N-9-fluorenylmethoxycarbonyl group (4 g; 2.8 mmol; 0.7 mmol.g$^{-1}$ theoretical load) is expanded in DMF (20 ml) for 15 minutes then the excess of DMF is removed by filtration. A solution of piperidine in DMF (20% v/v) is added to the resin and the mixture is stirred on the rotary shaker for 30 minutes at ambient temperature. The resin is filtered then washed using DMF, DCM and DMF then the reaction is repeated once. After 30 minutes, the resin is filtered and the final washing is carried out using 3 sequences of DMF, dichloromethane and MeOH then Et$_2$O. The resin is then dried under vacuum using a vane pump for 6 hours.

General Protocol for the Coupling of Basic Carboxylic Acid from which R$_3$ Derives A solution of basic carboxylic acid from which preactivated R$_3$ (HOBt ester) derives is prepared by firstly mixing the acid hydrochloride (4.15 mmol) and HOBt (0.635 g; 4.15 mmol) in DMF (3 ml) as well as a solution of DIEA (4.15 mmol) in DMF (3 ml) and stirring for 15 minutes at ambient temperature. DIC (0.523 g; 4.15 mmol) in DMF (4 ml) is then added to the mixture and the medium is stirred for 15 minutes at ambient temperature. During this time, the supported primary amine (1 g; 0.83 mmol; 0.83 mmol.g$^{-1}$ theoretical load) is expanded in DMF (30 ml) for 30 minutes without stirring. The preactivated acid solution (4.15 mmol) is now added to the resin and the mixture stirred on the rotary shaker for 6 hours at ambient temperature. The resin is then filtered and washed using 3 sequences of DMF, dichloromethane and MeOH then Et$_2$O. The resin is then dried under vacuum using a vane pump for 6 hours.

When the carboxylic acid is not in the form of the hydrochloride, the solution of DIEA in DMF is not necessary and must be replaced by DMF alone.

(5-[1-benzyl-2-(4-methylpiperazin-1-yl)-2-oxoethyl-carbamoyl]-5-(tert-butoxy-carbonyl aminopentylcarbamoyl)-methyl)-1-methylpyridinium iodide 17a Compound 17a is obtained after quaternarization using methyl iodide and Hofmann elimination in accordance with the general protocol.
Yield: 121 mg of white solid (75%).
HPLC: 81% dionex, gradient A, Rt 21.9 minutes.

Mass ($C_{33}H_{49}N_6O_5$=609.81; (ESI-TOF) monoisotopic m/z, calculated for [M]⁺: 609.3764 g/mol, observed: 609.3073)

¹H NMR (200 MHz, CDCl₃) 9.52 (brd s, 1H, Py2); 8.83 (d, J=7.1 Hz, 1H, NH); 8.80 (d, J=5.6 Hz, 1H, Py4); 8.51 (d, J=7.8 Hz, 1H, Py6); 7.96 (t, J=7.3 Hz, 1H, Py5); 7.54 (d, J=7.8 Hz, 1H, NH); 7.30-7.15 (m, 5H, Ph); 5.05 (q, J=7.6 Hz, 1H, HαLys); 4.52 (s, 3H, PyMe); 4.98 (m, 1H, HαPhe); 4.26-4.33 (m, 2H, CH₂Py); 3.84 (d, J=14.7 Hz, 1H, NH); 3.46-3.34 (m, 3H, H₂,₆piperazine & HβPhe); 3.17-2.89 (m, 9H, HεLys, HβPhe & H₂,₆piperazine); 2.32-2.18 (m, 4H, H₃,₅piperazine); 2.18 (s, 3H, MeN); 1.81 (m, 2H, HβLys); 1.48-1.42 (m, 13H, HχLys, HδLys & tBu).

¹³C NMR (50 MHz, CDCl₃) 171.65 ($C_{amide}$); 170.11 ($C_{amide}$); 168.87 ($C_{amide}$); 156.58 ($C_{carbam}$); 146.68 ($C_6py$); 143.12 ($C_4py$); 138.37 ($C_2py$); 136.80 ($C_1ph$); 130.07 ($C_{3,5}ph$); 128.94 ($C_{2,6}ph$); 127.77 ($C_4ph$); 127.35 ($C_5py$); 126.28 ($C_3py$); 79.39 (CtBu); 55.37 ($C_{pyMe}$); 55.14 (CαLys); 54.64 ($C_{2,6}$piperazine); 50.14 (CαPhe); 49.36 (CH₂py); 46.18 ($C_{MeN}$); 45.81 ($C_{3,5}$piperazine); 42.21 ($C_{3,5}$piperazine); 40.61 ($C_β$Phe); 39.51 ($C_ε$Lys); 31.64 ($C_β$Lys); 29.72 ($C_δ$Lys); 28.90 (CtBu); 23.60 ($C_χ$Lys)

General Protocol for the Deprotection of the Boc Group on the ε Nitrogen of Lysine and Elongation of the Side Chain.

The resin functionalized by an N-ε-tert-butyloxycarbonyl-lysine group (0.735 g) is expanded in 6 ml of DCM in a "peptide vessel" then a solution of TFA/DCM 3:1 (14 ml) is added. After deprotection for one hour at ambient temperature, the resin is filtered, and washed using 3 sequences of DMF, 10% DIEA (DCM), dichloromethane and MeOH then Et₂O. The resin is then dried under vacuum using a vane pump for 6 hours. The elongation of the side chain can be carried out in 2 stages, firstly by reacting the deprotected amine with p-nitrophenylchloroformate then displacing the leaving group p-nitrophenol by a diamine (for example: 1,4-diaminobutane, 1,12-diaminododecane etc.). Thus, the Boc-deprotected and dried amine (0.012 g; 0.01 mmol; 0.83 mmol.g⁻¹ theoretical load) is expanded in a minimum quantity of dry dichloromethane for 15 minutes in a Supelco syringe. 0.5 ml (0.1 mmol) of a solution of DIEA [0.2 M] in dry DCM/THF 1:1 is added to the suspension then 0.5 ml (0.1 mmol) of a solution of p-nitrophenylchloroformate [0.2 M] in dry DCM/THF 1:1. The reaction is carried out at ambient temperature for 2 hours. The resin is then filtered and washed with 2 sequences of dichloromethane and THF then 1 ml (0.2 mmol) of a solution of diamine [0.2 M] is added and the stirring is continued for 15 hours at ambient temperature. The resin is then filtered and washed using 3 sequences of DMF, dichloromethane and MeOH then Et₂O. The resin is then dried under vacuum using a vane pump for 6 hours.

General Protocol for the Coupling of the Fluorescent Lissamine Sulphonyl Chloride Group to the Supported Primary Amine.

The dry resin (0.3 g; 0.243 mmol; 0.81 mmol.g⁻¹ theoretical load) is expanded in a minimum quantity of DCM for 15 minutes in a flask equipped with a magnetic stirrer. 12 ml of a solution of DIEA [0.04 M] in DCM (0.48 mmol) is added to the suspension, then 12 ml of a solution of lissamine sulphonyl chloride [0.04 M] in DCM (0.48 mmol). The reaction is carried out at ambient temperature with slow stirring for 5 hour. The resin is then filtered and washed using 3 sequences of DMF, 10% AcOH (DCM), 10% DIPEA (DCM), dichloromethane and MeOH then 2 sequences of DMF and finally Et₂O. The resin is then dried under vacuum using a vane pump for 6 hours.

(5-[1-benzyl-2-(4-methylpiperazin-1-yl)-2-oxoethyl-carbamoyl]-5-(3',6'-bis(diethyl amino)-9 mL (2-sulphophenylxanthyl-4-sulphonyl)aminopentylcarbamoyl)-methyl)-1-methylpyridinium bis trifluoroacetate 22a Compound 22a is obtained after quaternarization using methyl iodide and Hofmann elimination in accordance with the general protocol. Cleavage makes it possible to obtain 182 mg of crude product in the form of dark violet solid. Purification is carried out by semi-preparative RP-HPLC. The crude mixture is solubilized in 7 ml of MeOH/H₂O 1:2 and 7 injections of 1 ml are carried out (gradient B).

Yield: 77 mg of violet solid (25%).

HPLC: 96% dionex, gradient A, Rt 25.0 min.

Mass ($C_{55}H_{70}N_8O_9S_2$, 2TFA-=1051.34+226.03=1277.37; (ESI-TOF) monoisotopic m/z, calculated for [M]⁺: 1050.5043 g/mol, observed: 525.7598)

¹H NMR (200 MHz, MeOD) 8.94 (brd s, 1H, Py2); 8.83 (d, J=5.6 Hz, 1H, Py4); 8.71 (d, J=1.5 Hz, 1H, liss); 8.51 (d, J=8.1 Hz, 1H, Py6); 8.16 (dd, J=2 Hz, J=8.1 Hz, 1H, liss); 8.06 (dd, J=6.1 Hz, J=7.8 Hz, 1H, Py5); 7.58 (d, J=7.8 Hz, 1H, liss); 7.40-7.15 (m, 5H, Ph); 6.95-7.21 (m, 6H, liss); 5.05 (m, 1H, HαLys hidden by HOD); 4.43 (s, 3H, PyMe); 4.30 (m, 1H, HαPhe); 3.95 (d, J=2.5 Hz, 2H, CH₂Py); 3.69 (t, J=6.7 Hz, 8H, liss); 3.20-3.60 (m, 7H, hidden by MeOH); 3.09-2.83 (m, 8H, HεLys, HβPhe, MeN & $H_{piperazine}$); 1.73 (m, 2H, HβLys); 1.42-1.58 (m, 4H, HγLys & HδLys); 1.33 (m, 12H, liss).

Another fraction is obtained corresponding to the isomer at the position of the sulphonamide group on the lissamine Yield: 20 mg of violet solid (6%).

Mass ($C_{55}H_{70}N_8O_9S_2$, 2TFA-=1051.34+226.03=1277.37; (ESI-TOF) monoisotopic m/z, calculated for [M]⁺: 1050.5043 g/mol)

HPLC: 80% dionex, gradient A, Rt 24.4 minutes.

¹H NMR (200 MHz, MeOD) 9.01 (brd s, 1H, Py2); 8.86 (d, J=6.1 Hz, 1H, Py4); 8.67 (s, 1H, liss); 8.55 (d, J=7.1 Hz, 1H, Py6); 8.27 (dd, J=1.7 Hz, J=7.8 Hz, 1H, liss); 8.08 (dd, J=6.4 Hz, J=8.3 Hz, 1H, Py5); 7.60 (d, J=7.8 Hz, 1H, liss); 7.40-7.25 (m, 5H, Ph); 6.95-7.20 (m, 6H, liss); 5.00 (m, 1H, HαLys hidden by HOD), 4.49 (s, 3H, PyMe); 4.30 (m, 1H, HαPhe); 3.98 (m, 2H, CH₂Py); 3.73 (q, J=7.1 Hz, 8H, liss); 3.20-3.60 (m, 5H, hidden by MeOH); 3.10-2.85 (m, 10H, HεLys, HβPhe, MeN & $H_{piperazine}$); 1.67 (m, 2H, HβLys); 1.35-1.45 (m, 4H, HγLys & HδLys); 1.35 (t, J=7.1 Hz, 12H, liss).

Compound 22b

Compound 22b is obtained after quaternarization using benzyl bromide and Hofmann elimination in accordance with the general protocol. Cleavage makes it possible to obtain 264 mg of crude product in the form of dark violet solid. Purification is carried out by semi-preparative RP-HPLC. The crude mixture is solubilized in 6 ml of MeOH and 6 1-ml injections are carried out (gradient C).

Yield: 44 mg of violet solid (20%).

HPLC: 95% dionex, gradient A, Rt 20.8 minutes.

Mass ($C_{71}H_{89}N_9O_9S_2$, 2TFA-=1276.67+226.03=1502.70; (ESI-TOF) monoisotopic m/z, calculated for [M]⁺: 1275.6250 g/mol, observed: 637.8349)

Another fraction is obtained corresponding to the isomer at the position of the sulphonamide group on the lissamine Yield: 16 mg of violet solid (7%).

HPLC: >95% dionex, gradient A, Rt 19.8 minutes.

Mass ($C_{66}H_{84}N_8O_9S_2$, 2TFA-=1197.57+226.03=1423.60; (ESI-TOF) monoisotopic m/z, calculated for [M]⁺: 1196.5778 g/mol)

Compound 22c

Compound 22c is obtained after quaternarization using benzyl bromide and Hofmann elimination in accordance with the general protocol. Cleavage makes it possible to obtain 264 mg of crude product in the form of dark violet solid. Purification is carried out by semi-preparative RP-HPLC. The crude mixture is solubilized in 6 ml of MeOH and 6 1-ml injections are carried out (gradient C).

Yield: 83 mg of violet solid (27%).

HPLC: 95% dionex, gradient A, Rt 20.0 minutes.

Mass ($C_{66}H_{84}N_8O_9S_2$, 2TFA-=1197.57+226.03=1423.60; (ESI-TOF) monoisotopic m/z, calculated for $[M]^+$: 1196.5778 g/mol, observed: 598.3161)

Another fraction is obtained corresponding to the isomer at the position of the sulphonamide group on the lissamine Yield: 28 mg of violet solid (9%).

HPLC: 85% dionex, gradient A, Rt 18.8 minutes.

Mass ($C_{66}H_{84}N_8O_9S_2$, 2TFA-=1197.57+226.03=1423.60; (ESI-TOF) monoisotopic m/z, calculated for $[M]^+$: 1196.5778 g/mol)

Example 1

Expression of the M1 Receptor Fused at its Amino-Terminal End to the EGFP Protein and Screening of Fluorescent Combinatorial Libraries I) Fusion of the Coding Sequence of the M1 Receptor to the EGFP The coding sequence of the human muscarinic M1 receptor (Genbank accession N°: X15263) is amplified by PCR using the primers:

```
Sense primer:
5' acc gcc gcc ggg atc tca gat ctc gga aag ggt ccc tgg (SEQ ID NO: 5)

Anti-sense primer:
5' gca gga cgc agg ctc gag tca gca ttg gcg ggaggg
(SEQ ID NO: 6)
```

This sequence is fused in phase with the peptide signal of the chicken alpha 7 sub-unit (Genbank accession N°: X52295) of the nicotinic acetylcholine receptor, which is amplified by PCR using the primers:

```
Sense primer:
5' ggt cgg ctg cgg ccg cat ggg cct ccg ggc gct
(SEQ ID NO: 7)

Anti-sense primer:
5' cca ggg acc ctt tcc gag atc tga gat ccc ggc ggc ggt (SEQ ID NO: 8)
```

The sequences obtained are cleaved by the enzymes BglII and Xho1 for the sequence of the M1 receptor, and by the enzymes Not1 and Bgl II for the peptide signal-EGFP fragment. These fragments are then placed in the KS vector opened by the enzymes Not1 and Xho1: The sequence SP-EGFP-M1 is then sub-cloned into the expression vector pCEP4 (Invitrogen) before being sent to be sequenced as described in Ilien et al. (*J. Neurochem.*, 2003, 85: 768-78). In this construction, the M1 receptor is truncated by 17 amino acids in its amino-terminal part, relative to its wild-type sequence, and a spacer arm 6 amino acids in length separates the GFP from the receptor.

II) Expression of the Recombinant Proteins

HEK 293 cells are transfected by the calcium phosphate precipitation method (Chen & Okayama 1987, Mol. Cell. Biol. 7: 2745-2752) by the construction pCEP4-SP-EGFP-M1. Stable lines are established by selection of the hygromycin-resistant transfected cells (100 μg/ml, Clontech). The cells are cultured in an MEM medium (Gibco) supplemented by 10% foetal calf serum (Sigma), penicillin (100 units/ml), streptomycin (100 μg/ml) and glutamine (4 mM).

III) Measurements of the Expression of the M1 Receptor Fused to the EGFP, by Fluorimetry The fluorescence experiments are carried out in a 1 ml cuvette provided with a magnetic stirring system and placed in a Fluorolog spectrofluorimeter (SPEX) equipped with an Xe 450 W lamp (Osram) and Spex 1680 0.22 m (excitation) and Spex 1681 0.22 m (emission) monochromators. The cells are suspended in a physiological buffer: Hepes 10 mM, NaCl 137.5 mM, $MgCl_2$ 1.25 mM, $CaCl_2$ 1.25 mM, KCl 6 mM, glucose 5.6 mM, $NaH_2PO_4$ 0.4 mM, BSA 0.1% (W/v), pH 7.4.

The whole cells are harvested after treatment with trypsin-EDTA (1× Gibco) at ambient temperature. The cells are centrifuged for 5 minutes at 100 g and resuspended at a concentration of 1 to $2.10^6$ cells/ml in the physiological buffer.

An emission spectrum of the cells transfected by pCEP4-SP-EGFP-M1 is shown in FIG. 1. A spectrum is produced before each screening. The spectra clearly show the EGFP signal, indicating that these cells express EGFP clearly in comparison with the non-transfected cells.

IV) Screening of Collections of Fluorescent Compounds on the HEK Line Expressing the M1 Receptor Fused to the EGFP IV.1. Screening Procedure The distribution of ligands and cells is carried out using an automated pipetter-distributer (Biomek 2000) and the fluorescence is measured in a spectrofluorimeter (Victor II, Perkin Elmer).

98 μl of physiological buffer, 2 to 4 μl of fluorescent ligand (corresponding to a compound labelled according to the present invention) and 100,000 cells (100 μl) of a cell suspension are distributed, chronologically, into a black 96-well plate (Labsystem).

The fluorescent ligands are screened at a final concentration varying from 500 nM to 1 μM. These ligands are dissolved in DMSO, the final concentration of which in the test varies between 1 and 2%. The cells are distributed from a reservoir, in which the cells are kept in suspension by alternating aspiration and expulsion carried out by the automated device before each distribution. In order to mix all of the compounds, the robot aspirates and expels a volume of 50 μl i.e. half of the wells once. The plate is then incubated for 10 minutes at ambient temperature, then centrifuged for 5 minutes at 100 g. It is then placed in the Victor fluorescence detector. The EGFP is excited at 465±7 nm and its emission is measured at 510±7 nm, for 2 seconds, 0.8 mm from the bottom of the plate.

In a 96-well plate, 16 wells serve as a control and 80 fluorescent ligands are tested, i.e. one per well. The emission of the EGFP (510 nm) from each of the wells treated is compared with the average fluorescence of the EGFP (510 nm) from the 16 control wells. A fluorescence extinction percentage is thus calculated and corresponds to the identification criterion for the leads.

Figure 2:
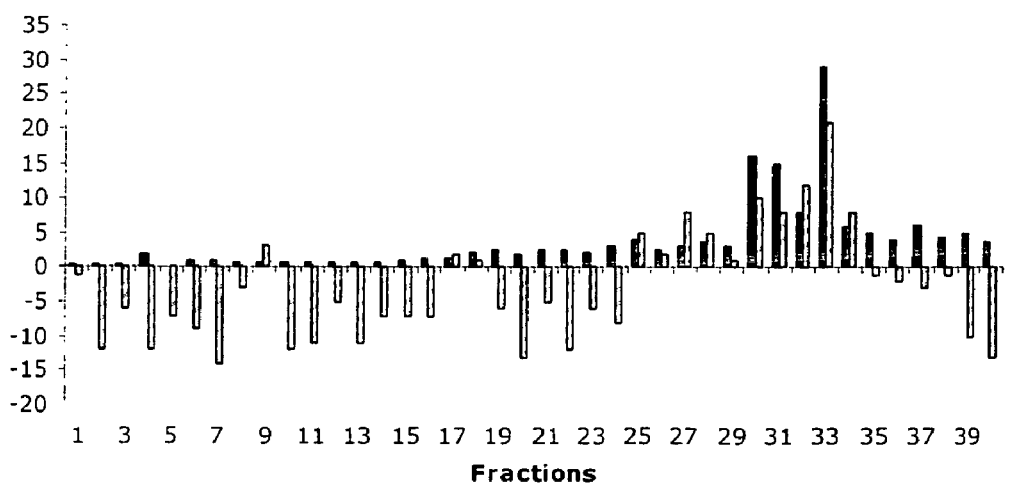
FIG. 2 represents the comparison of the absorbances at 220 nm and fluorescence resonance energy transfer (FRET) percentages on the different fractions of purified fluorescent ligand (see Example 1). The black rectangles represent the absorbance at 220 nm and the hatched rectangles the FRET percentage.

400 fluorescent ligands were tested according to this protocol, forty ligands were identified as potential ligands, called leads. The two ligands which produced the highest fluorescence extinction percentage (at 510 nm) were re-synthesized and purified per fraction. Each fraction was tested, on the one hand by binding to cells expressing the M1 receptor fused to EGFP and on the other hand by absorbance (220 nm). This experiment (FIG. 2) demonstrates that this is the principal fluorescent synthesis product, which induces the fluorescence extinction of the EGFP.

IV.2. Confirmation of the Leads and Structure of the Detected Ligands

Figure 3A:
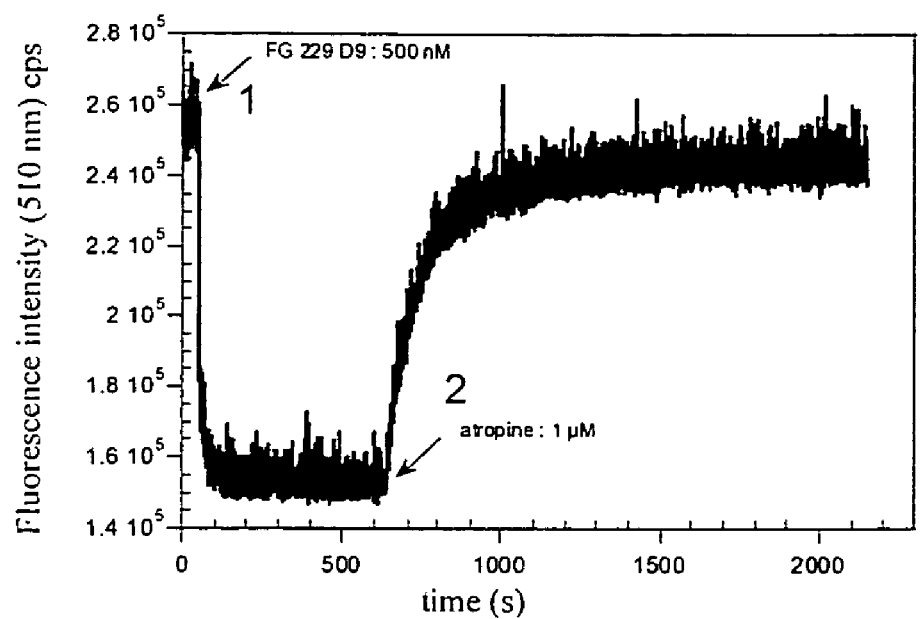
FIGS. 3A and 3B represent the measurement in real time of the transfer of energy between the purified fluorescent ligand 500 nM (FIG. 3A, 1), 100 nM (FIG. 3B, 3) and the M1-EGFP receptor and the reversal of this bond either by an excess of the same unlabelled ligand (FIG. 3B, 4), or by a known antagonist, atropine (FIG. 3A, 2). The time in seconds is shown along the x-axis and the fluorescence intensity at 510 nm (counts per second) along the y-axis, the excitation taking place at 470 nm.
Figure 3B:
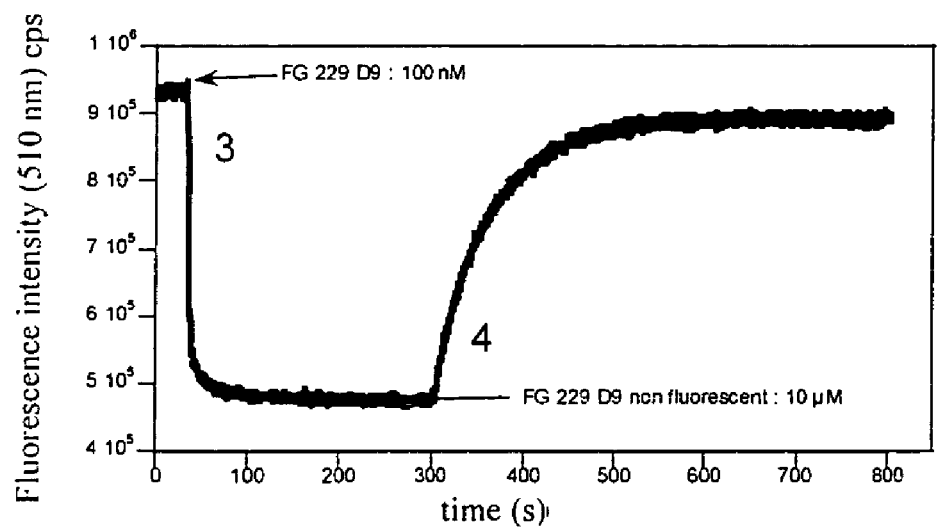
Figure 4:
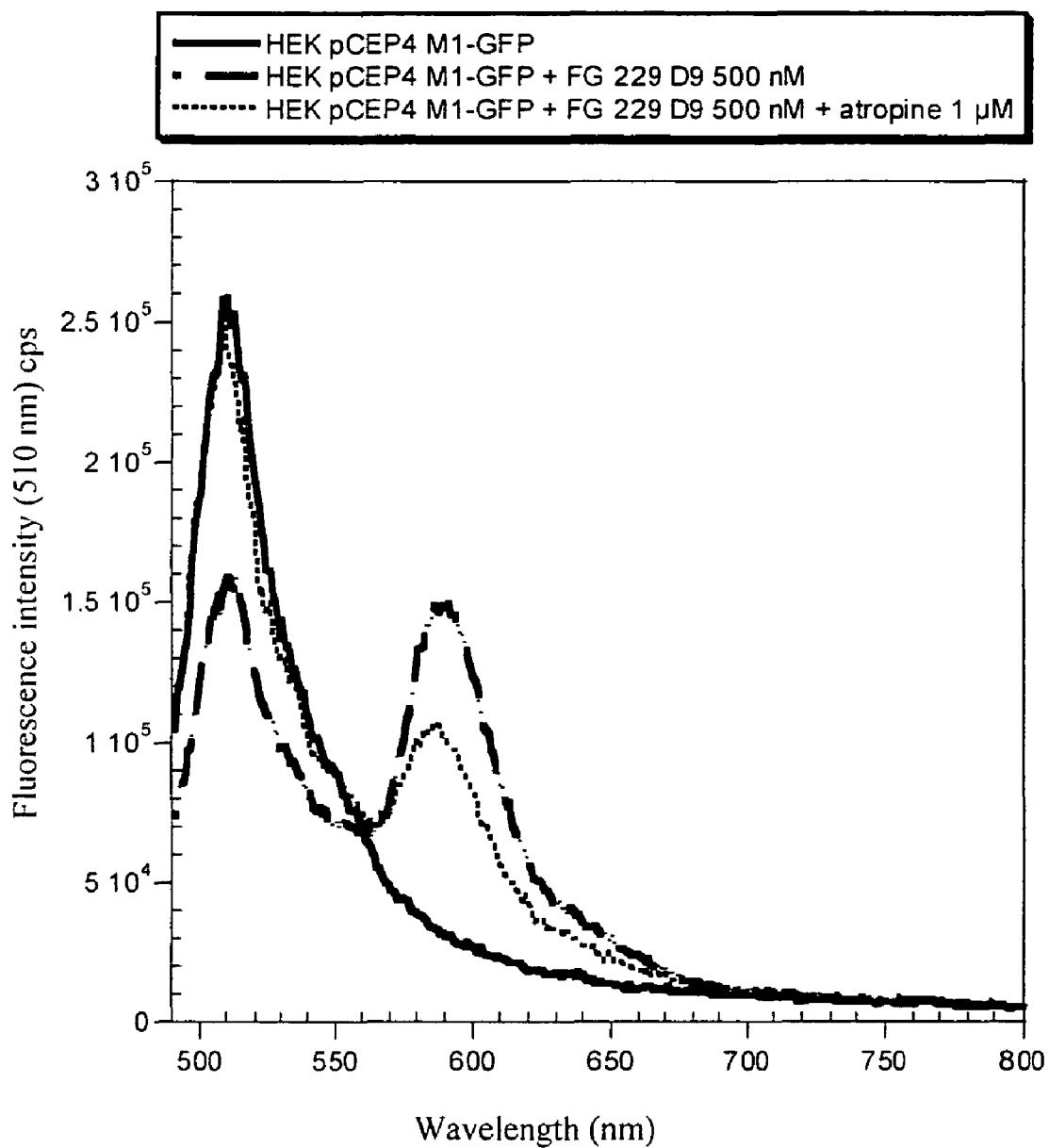
FIG. 4 represents the emission spectra of HEK 293 cells in suspension expressing the construction pCEP4-M1-EGFP. The fluorescence intensity expressed in counts per second (cps) is represented on the y-axis and the emission wavelength (nm) on the x-axis. The solid-line curve represents the emission spectrum of the cells expressing pCEP4-M1-EGFP; the dashed-line curve represents the emission spectrum of the cells expressing pCEP4-M1-EGFP in the presence of fluorescent ligand; the dotted-line curve represents the emission spectrum of the cells expressing pCEP4-M1-EGFP in the presence of fluorescent ligand and known antagonist, atropine.

The leads identified during the screening are confirmed with the spectrofluorimer (equipment previously described). The measurements are carried out in a 1-ml cuvette with a suspension of 1 to $2.10^6$ cells/ml of physiological buffer (same composition as mentioned previously) (see FIGS. 3A and 3B; FIG. 4).

FIG. 4 clearly shows the fluorescence extinction of the EGFP at 510 nm, due to the energy transfer to the fluorescent ligand. A return to a maximum emission of the EGFP at 510 nm is observed. The fluorescent ligand is driven from its binding site by the antagonist. The energy transfer to the fluorescent ligand is interrupted and the emission of the EGFP is once again maximum.

One of the preferred ligands discovered by screening, named FG 229 D9, possesses the following structure:

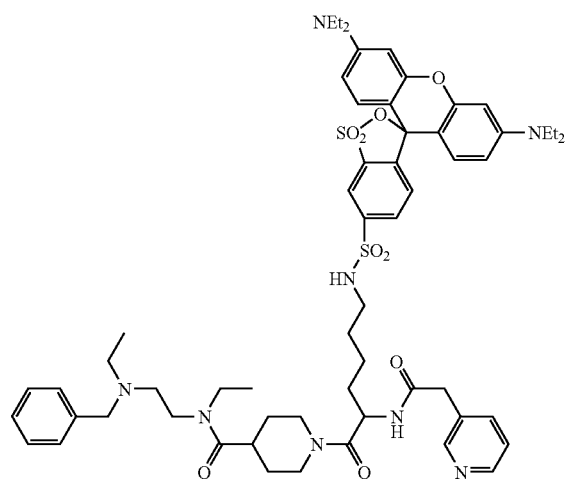

Such a compound corresponds to a compound of formula (I) according to the invention, in which n=0, p=4, $R_1$ and $R'_1$ represent an ethyl group, $R_2$ represents the side chain of isonipecotinic acid, $R_3$ represents

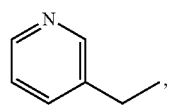

$R_4$ represents a benzyl group and A represents a lissamine derivative.

The biological activity of this compound in the FRET test is illustrated in FIGS. 3 and 4.

Example 2

Expression of the GPR 50 Orphan Receptor Fused at its Amino-Terminal End to the EGFP Protein and Screening of Fluorescent-Combinatorial Library I) Fusion of the Coding Sequence of the Orphan GPR 50 Receptor to the EGFP The coding sequence of the GPR50 receptor (Genbank accession N°: U 52219) is placed in the vector pCEP4-SP-EGFP (previously described in Example 1). These 3' and 5' ends of the coding sequence contain sequences complementary to the 5' and 3' ends of the pCEP4-SP-EGFP vector digested by Fse1. These complementary sequences were introduced into the primers used during the PCR (underlined sequences) in order to amplify the coding sequence of the receptor.

```
Sense primer:
5' G GCC GGG GCC GGG ACC CCC TAT GGC TGT ATT GGC
(SEQ ID NO: 1)

Anti-sense primer:
5' CTC GTT CTC GTT GGA TCA CAC AGC CAT TTC
ATC AGG ATC (SEQ ID NO: 3)
```

This method of directional insertion of PCR fragments into a vector, does not involve any restriction enzyme (Aslanidis C et al.; 1990, *Nucleic Acids Res.* 18, 6069-6074, Haun R. S. et al.; 1992, *BioTechniques* 13, 515-518).

In the construction pCEP4-SP-EGFP-GPR50, a spacer arm 6 amino acids in length separates the EGFP from the receptor. As for the receptor, it possesses a amino-terminal end 30 amino acids in length, which has been truncated by 9 amino acids relative to its wild-type sequence.

II) Expression of the Recombinant Proteins

HEK 293 cells are transfected by the calcium phosphate precipitation method (Chen & Okayama 1987, Mol. Cell. Biol. 7: 2745-2752) by the construction pCEP4-SP-EGFP-GPR50. Stable lines are established by selection of hygromycin-resistant transfected cells (500 μg/ml, Clontech). The cells are cultured in an MEM medium (Gibco) supplemented by 10% foetal calf serum (Sigma), penicillin (100 units/ml), streptomycin (100 μg/ml) and glutamine (4 mM).

III) Measurements of the Expression of the Receptor GPR50 Fused to EGFP, by Fluorimetry The fluorescence experiments are carried out in a 1 ml cuvette provided with a magnetic stirring system and placed in a Fluorolog spectrofluorimeter (SPEX) equipped with a Xe 450 W lamp (Osram) and Spex 1680 0.22 m (excitation) and Spex 1681 0.22 m (emission) monochromators. The cells are suspended in a physiological buffer: Hepes 10 mM, NaCl 137.5 mM, $MgCl_2$ 1.25 mM, $CaCl_2$ 1.25 mM, KCl 6 mM, glucose 5.6 mM, $NaH_2PO_4$ 0.4 mM, BSA 0.1% (W/v), pH 7.4.

The whole cells are harvested after treatment with trypsin-EDTA (1× Gibco) at ambient temperature. The cells are centrifuged for 5 minutes at 100 g and resuspended at a concentration of 1 to $2.10^6$ cells/ml in the physiological buffer.

Figure 5:
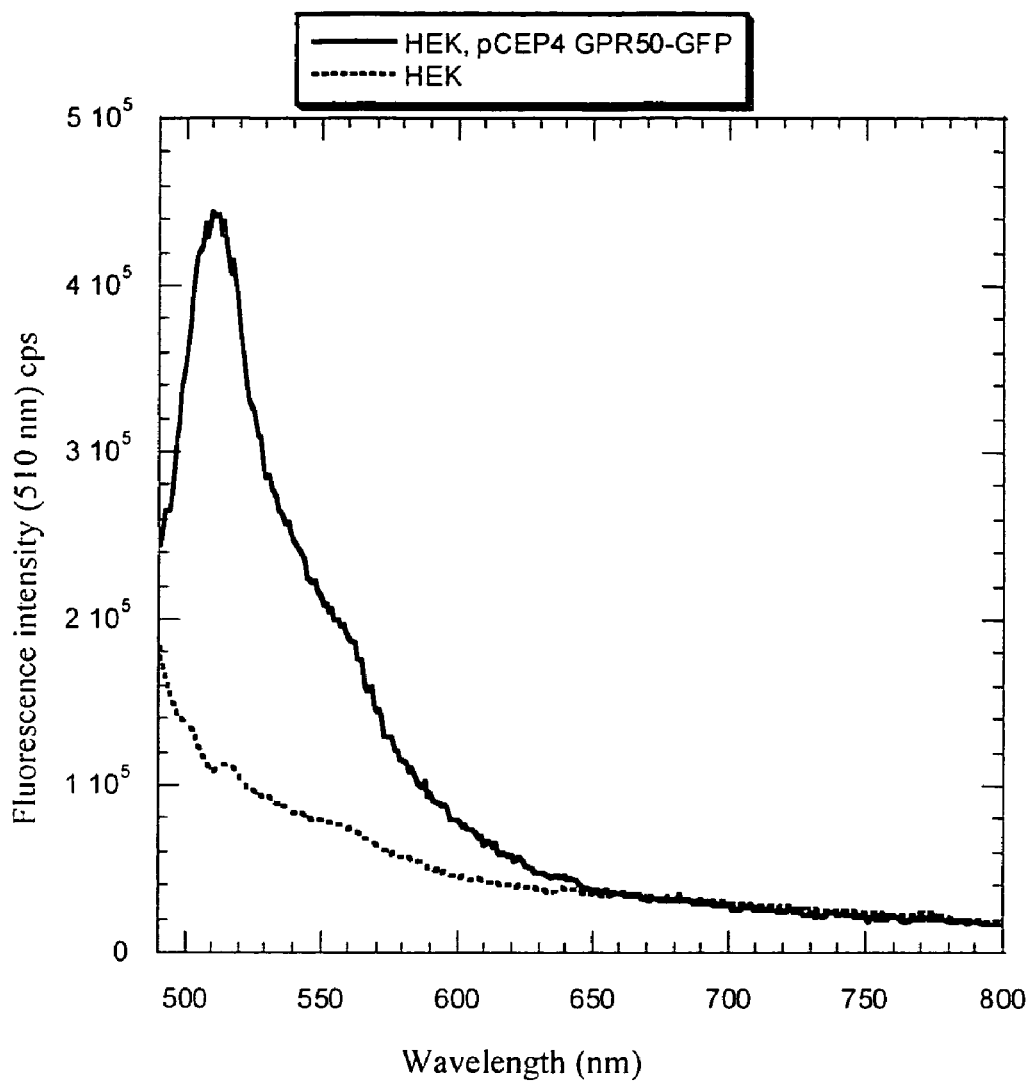
FIG. 5 represents an emission spectrum of HEK 293 cells transfected by the construction pCEP4-SP-EGFP-GPR50 (see Example 2 hereafter). The y-axis corresponds to the wavelength (in run) and the x-axis to the fluorescence intensity (in cps). The solid-line curve corresponds to the HEK cells expressing pCEP4-SP-EGFP-GPR50 and the dotted-line curve to the non-transfected HEK cells.

An emission spectrum of the cells transfected by pCEP4-SP-EGFP-GPR50 is shown in FIG. 5. A spectrum is produced before each screening. The spectra clearly show the EGFP signal, indicating that these cells express EGFP clearly in comparison with the non-transfected cells.

IV) Screening of Collections of Fluorescent Compounds on the HEK Line Expressing the GPR50 Receptor Fused to EGFP IV.1. Screening Procedure The distribution of the ligands and of the cells is carried out using an automated pipetter-distributer (Biomek 2000) and the fluorescence is measured in a spectrofluorimeter (Victor II, Perkin Elmer).

98 μl of physiological buffer, 2 to 4 μl of fluorescent ligand and 100,000 cells (100 μl) of a cell suspension are distributed, chronologically, into a black 96-well plate (Labsystem).

The fluorescent ligands are screened at a final concentration varying from 500 nM to 1 μM. These ligands are dissolved in DMSO, the final concentration of which in the test varies between 1 and 2%. The cells are distributed from a reservoir, in which the cells are kept in suspension by alternating aspiration and expulsion carried out by the automated device before each distribution. In order to mix all of the compounds, the robot aspirates and expels half of the wells once. The plate is then incubated for 10 minutes at ambient temperature, then centrifuged for 5 minutes at 100 g. It is then placed in the Victor fluorescence detector. The EGFP is excited at 465±7 nm and its emission is measured at 510±7 nm, for 2 seconds, 0.8 mm from the bottom of the plate.

In a 96-well plate, 16 wells serve as a control and 80 fluorescent ligands are tested, i.e. one per well. The emission of the EGFP (510 nm) from each of the wells treated is compared with the average fluorescence of the EGFP (510 nm) from the 16 control wells. A fluorescence extinction percentage is thus calculated and corresponds to the criterion of identification of the leads.

Three thousand fluorescent ligands were tested according to this protocol.

IV.2. Confirmation and Structure of the Potential Leads

The binding of certain molecules was verified with the spectrofluorimeter (equipment previously described (see Example 1)). The measurements are carried out in a 1 ml cuvette with a suspension of 1 to $2.10^6$ cells/ml of physiological buffer (composition mentioned in Example 1).

Figure 6:
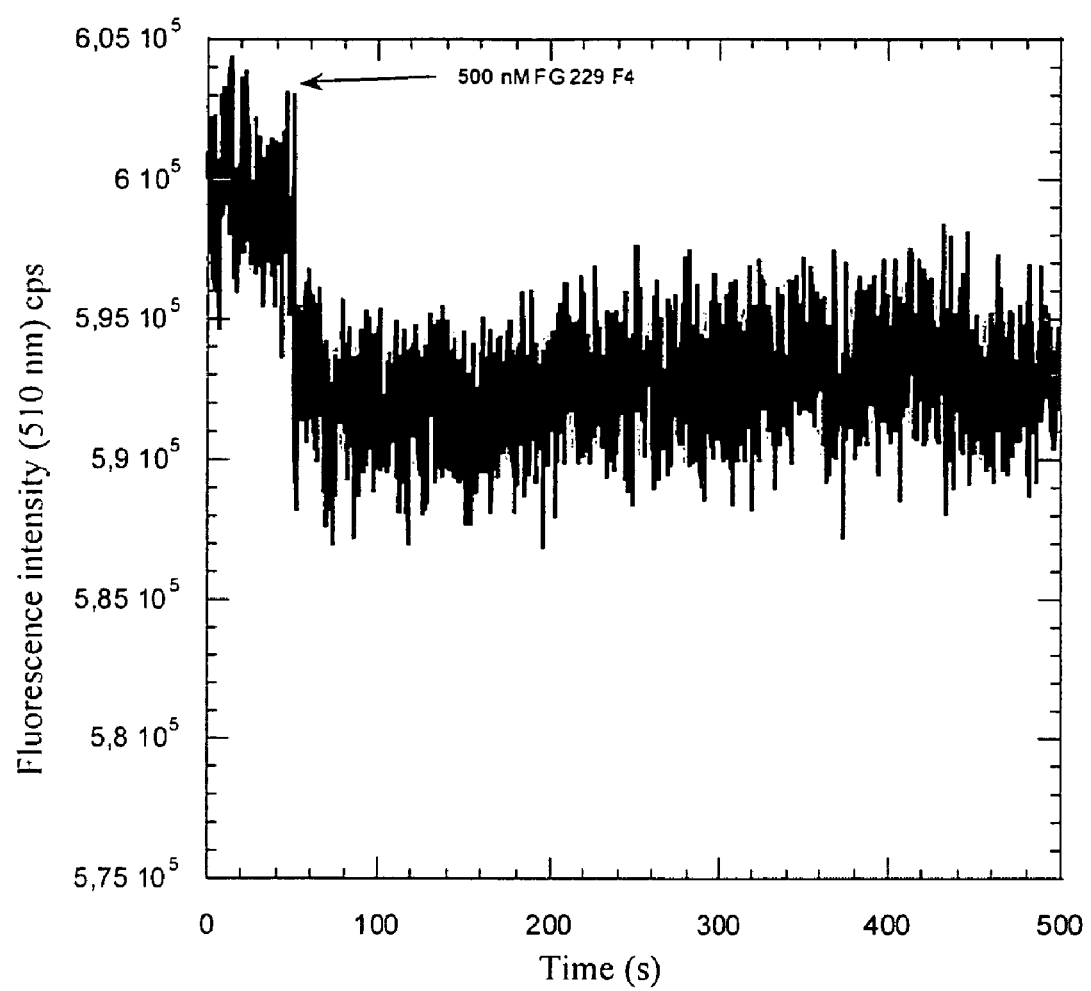
FIG. 6 represents the measurement in real time of the transfer of energy between the fluorescent ligand FG 229 F4 at 500 nM (1) and the GPR50-EGFP receptor. The time in seconds is represented along the x-axis and the fluorescence intensity at 510 nm (counts per second) along the y-axis, the excitation taking place at 470 nm (a low energy transfer of 2% can be measured).

One of the preferred ligands discovered by screening (FG 229 F4; see FIG. 6) has the following structure:

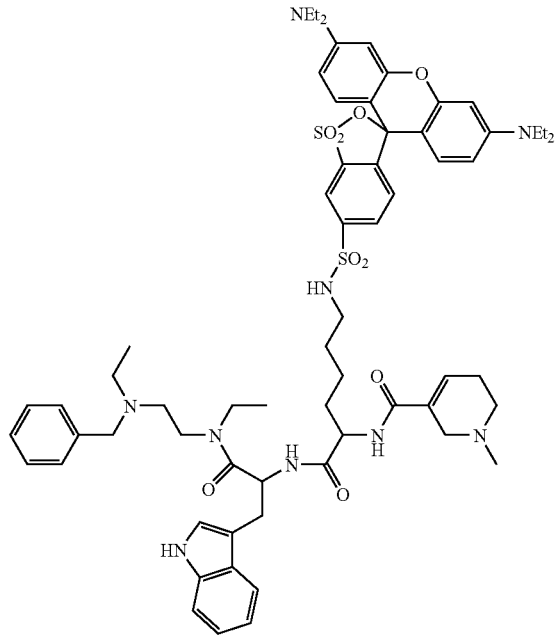

Such a compound corresponds to a compound of formula (I) according to the invention, in which n=0, p=4, $R_1$ and $R'_1$ represent an ethyl group, $R_2$ represents the tryptophan side chain, $R_3$ represents

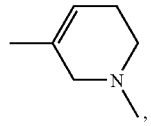

$R_4$ represents a benzyl group and A represents a lissamine derivative.

Example 3

Expression of the mGluR8 Receptor Fused at its Amino-Terminal End to the GFP Protein and Screening of Fluorescent Combinatorial Libraries I) Fusion of the Coding Sequence of the mGluR8 Receptor to GFP The coding sequence of the type 8 metabotropic glutamate receptor (mGluR8) (Genbank accession No.: P70579) is placed in the vector pcDNA6 (Invitrogen) downstream of the coding sequence for the GFP protein, which is itself placed downstream of the sequence coding for the peptide signal of the chicken alpha 7 sub-unit of the nicotinic acetylcholine receptor (corresponding to the amino acid sequence 1 to 25 of the protein sequence described in Genbank accession No.: X52295). The construction obtained is called pcDNA6-SP-GFP-mGluR8.

In the construction pcDNA6-SP-GFP-mGluR8, a spacer arm 6 amino acids in length separates the GFP from the receptor. As for the receptor, its amino-terminal end composed of 550 amino acids has been truncated by 547 amino acids. In this construction, there are therefore 9 amino acids which separate the GFP from the first transmembrane domain of the receptor.

II) Expression of the Recombinant Proteins

HEK 293 cells are transfected by a lipofectamine 2000 transfection agent (Invitrogen) according to the supplier's instructions with the construction pcDNA6-SP-GFP-mGluR8. Stable lines are established by selection of the transfected blasticidin-resistant cells (5 μg/ml, Invivogen). The cells are cultured in an MEM medium (PAA) containing L-glutamine (2 mM) and supplemented with 10% foetal calf serum (PAA), penicillin (100 units/ml), streptomycin (100 μg/ml).

III) Measurements of the Expression of the mGluR8 Receptor Fused to GFP, by Fluorimetry The fluorescence experiments are carried out in a 1 ml cuvette provided with a magnetic stirring system and placed in a Fluorolog-3 spectrofluorimeter (Jobin-Yvon Horiba). The cells are suspended in a physiological buffer: Hepes 10 mM; NaCl 137.5 mM; $MgCl_2$ 1.25 mM; $CaCl_2$ 1.25 mM; KCl 6 mM; glucose 5.6 mM; $NaH_2PO_4$ 0.4 mM; BSA 0.1% (W/v) pH 7.4.

The whole cells are harvested after treatment with PBS (PAA), EDTA 5 mM at ambient temperature. The cells are centrifuged for 5 minutes at 100 g and resuspended at a concentration of 1 to $2.10^6$ cells/ml in the physiological buffer.

Figure 7:
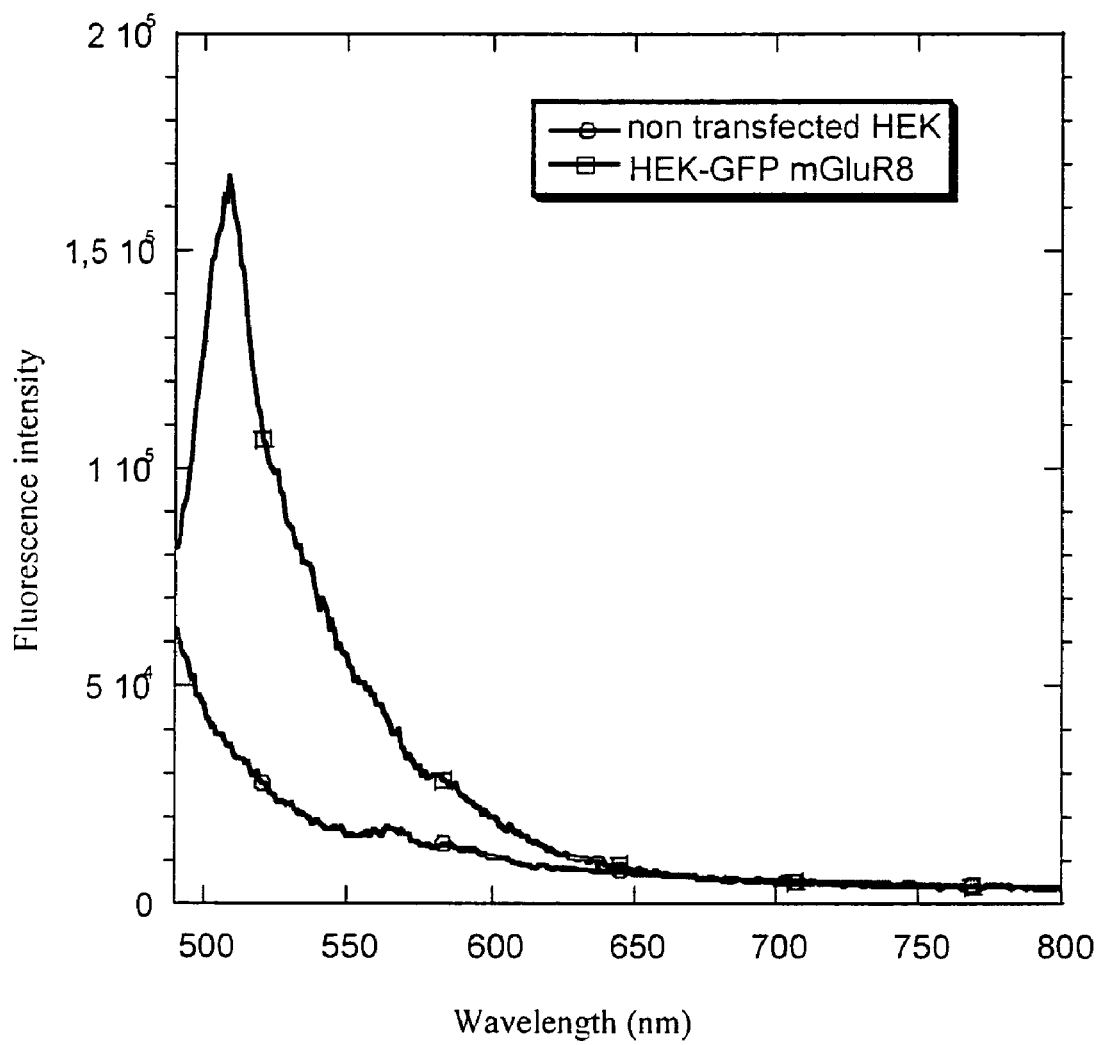
FIG. 7 represents an emission spectrum of HEK 293 cells transfected by the construction pcDNA6-SP-GFP-mGluR8 (see Example 3 hereafter). The y-axis corresponds to the wavelength (in nm) and the x-axis to the fluorescence intensity (in cps). The dotted-line curve corresponds to the HEK cells expressing pcDNA6-SP-GFP-mGluR8 and the solid-line curve to the non transfected HEK cells.

An emission spectrum of the cells transfected by the pcDNA-SP-GFP-mGluR8 is shown in FIG. 7. A spectrum is produced before each screening. The spectra clearly show the GFP signal, indicating that these cells express GFP clearly in comparison with the non transfected cells.

IV) Screening of Collections of Fluorescent Compounds on the HEK Line Expressing the mGluR8 Receptor Fused to GFP IV.1. Screening Procedure Twenty-four hours before the screening, the cells are seeded in 96-well plates. At the time of the experiment, the wells are rinsed out and the cells incubated in a physiological buffer the composition of which is described in paragraph III. The fluorescent ligands to be tested are distributed over the cells by the Flexstation (Molecular Devices) which follows the evolution of the fluorescence of GFP (excitation 475+/−8 nm, emission 510+/−8 nm) over time.

The fluorescent ligands are screened at a final concentration varying from 500 nM to 1 µM. These ligands are dissolved in DMSO, the final concentration of which in the test varies between 1 and 2%. A fluorescence extinction percentage of GFP is calculated for each well and corresponds to the identification criterion for the leads.

Approximately 800 fluorescent ligands originating from the combinatorial library described in the present invention were tested according to this protocol, one ligand was identified as a potential ligand of mGluR8.

IV.2. Confirmation of the Leads and Structure of the Ligands Detected

Figure 8:
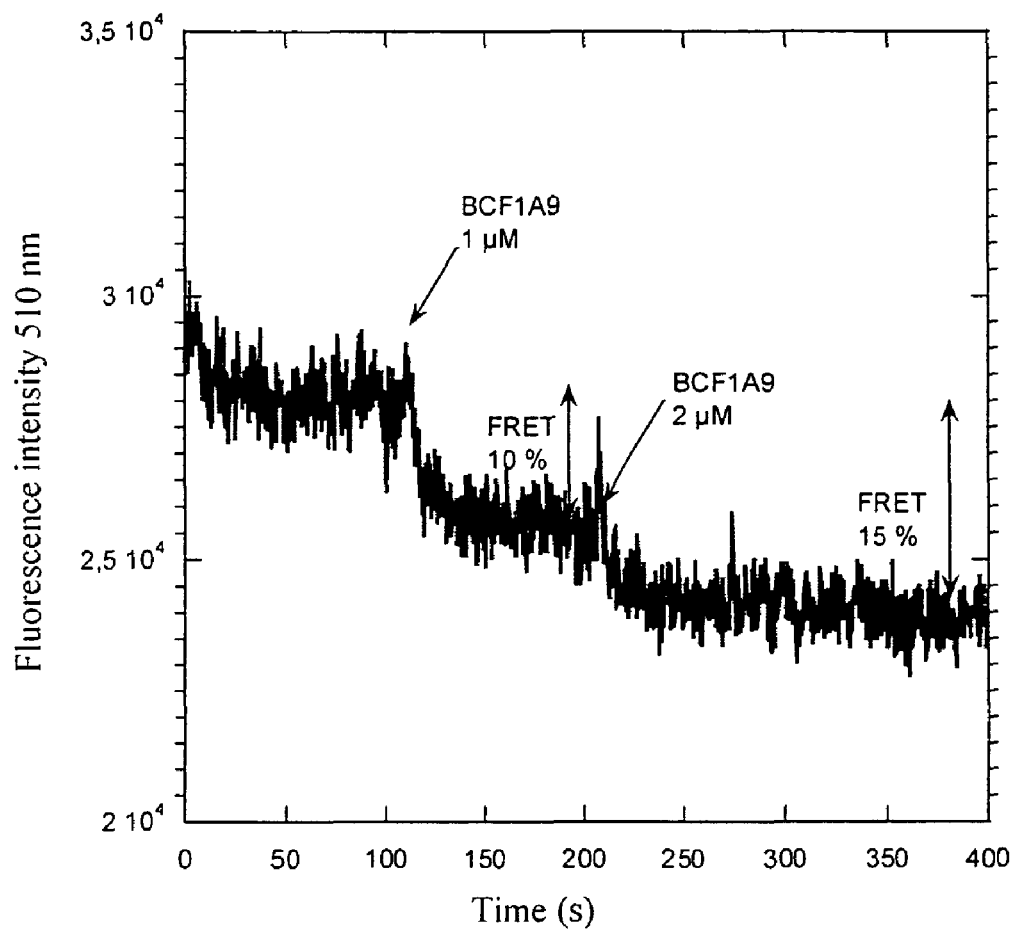
FIG. 8 represents the measurement in real time of the transfer of energy between the fluorescent ligand BCF1-A9 and the mGluR8-GFP receptor. The position of the arrows indicates the successive addition of BCF1A9. The time in seconds is represented along the x-axis and the fluorescence intensity at 510 nm (counts per second) along the y-axis, the excitation taking place at 475 nm (an energy transfer of 10 and 15% is measured).

The leads identified during the screening are confirmed with the spectrofluorimer (equipment previously described). The measurements are carried out in a 1-ml cuvette on HEK cells expressing the GFP-mGluR8 receptor, diluted in physiological buffer (same composition as mentioned previously). FIG. 8 illustrates the fluorescence extinction kinetics of the GFP during the interaction of a fluorescent ligand called BCF1A9 with the GFP-mGluR8 receptor.

Example 4

Expression of the Glucagon-Like Peptide-1 (GLP-1) Receptor Fused at its Amino-Terminal End to the GFP Protein and Screening of Fluorescent Combinatorial Library I) Fusion of the Coding Sequence of the GLP-1 Receptor to GFP A fluorescent GLP-1R receptor is obtained by fusion of part of its coding sequence to that of GFP. The coding sequence of the GLP-1 receptor (Genbank accession No.: NM_002062) is placed in a pcDNA6 vector downstream of the coding sequence of the autofluorescent GFP protein, which is itself placed downstream of the coding sequence for the peptide signal of the chicken alpha 7 sub-unit of the nicotinic acetylcholine receptor (corresponding to the amino acid sequence 1 to 25 of the sequence of the protein described in the Genbank accession No.: NP_989512). In the construction thus obtained, called pcDNA6-SP-GFP-GLP1R, a spacer arm corresponding to the sequence coding for two amino acids separates the GFP from the receptor. As for the receptor, a version truncated by 134 amino acids in its amino-terminal part was used for this study. This variant of the receptor possesses the characteristic of no longer allowing the binding of its endogenous ligand, the peptide related to Glucagon, GLP-1.

II) Expression of the Recombinant Proteins

HEK 293 cells are transfected by a lipofectamine 2000 transfection agent (Invitrogen) according to the supplier's instructions with the construction pcDNA6-SP-GFP-GLP-1R. Stable lines are established by selection of the blasticidin-resistant transfected cells (5 µg/ml, Invivogen). The cells are cultured in an MEM medium (PAA) containing L-glutamine (2 mM) and supplemented with 10% foetal calf serum (PAA), penicillin (100 units/ml) and streptomycin (100 µg/ml).

III) Measurements of the Expression of the GLP-1 Receptor Fused to GFP, by Fluorimetry Measurements of the expression of the GLP-1 receptor fused to GFP by fluorimetry are carried out as described previously in Example 3.

IV) Screening of Collections of Fluorescent Compounds on the HEK Line Expressing the GLP1R Receptor Fused to GFP The procedures for screening and confirmation of the leads were carried out as previously described in Example 3.

The invention claimed is:
1. A compound of the following formula (I):

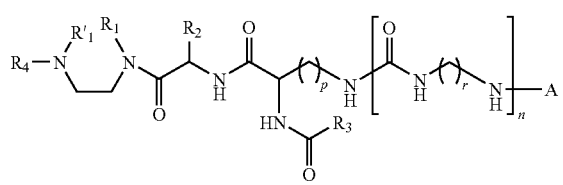

(I)

wherein:
n is equal to 0 or 1,
p represents an integer varying from 1 to 6,
r represents an integer varying from 1 to 12,
$R_1$ and $R'_1$ represent independently of each other an atom or a group selected from the group consisting of: a hydrogen atom, an alkyl group comprising from 1 to 6 carbon atoms, and an aromatic group,
or

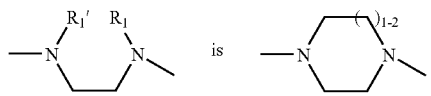 is 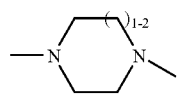

and the

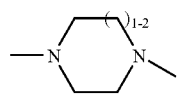

is optionally substituted with one group selected from the group consisting of: an alkyl group comprising from 1 to 6 carbon atoms and an aromatic group, $R_2$ represents a side chain of an amino acid or an amino acid derivative,
$R_3$ represents a group derived from a carboxylic acid, carrying a basic entity, selected from the group consisting of:

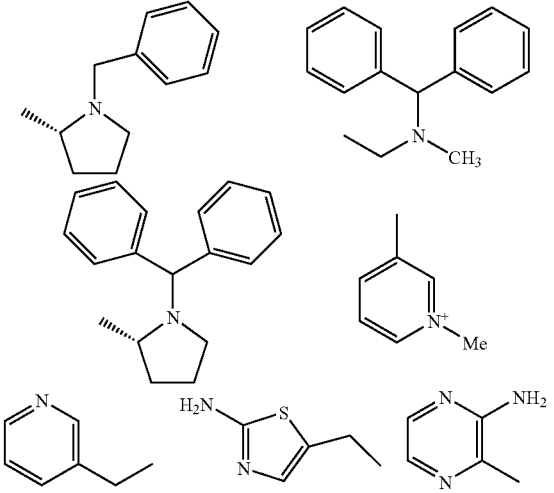

$R_4$ represents an alkyl group comprising from 1 to 10 carbon atoms, a phenyl group substituted by an alkyl group comprising from 1 to 10 carbon atoms, and
A represents a hydrogen atom, a protective group or a tracer group selected from the group consisting of: a fluorophore, a dye or a "quencher".

2. The compound of claim 1, wherein $R_2$ represents the side chain of an amino acid or amino acid derivative selected from the group consisting of: alanine, glutamine, leucine, glycine, tryptophan, β-alanine, phenylalanine, 4-chloro-phenylalanine, isonipecotinic acid, 4-aminomethylbenzoic acid, 3-tetrahydroisoquinolinic acid and free or benzylated histidine.

3. The compound of claim 1, wherein n is equal to 0.
4. The compound of claim 1, wherein n is equal to 1.
5. The compound of claim 3, wherein A represents a hydrogen atom or a protective group.
6. The compound of claim 5, corresponding to one of the following formulae:

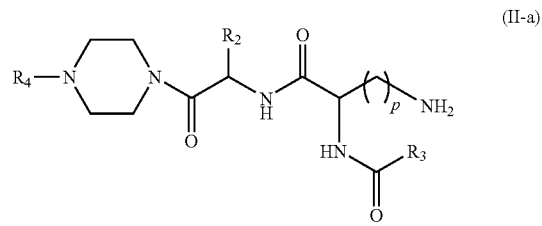

(II-a)

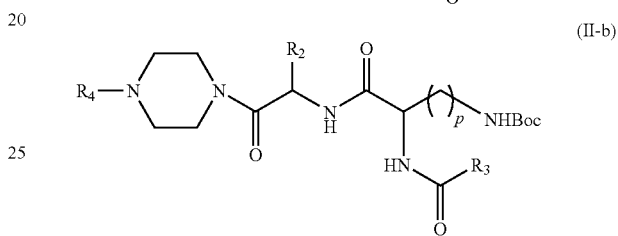

(II-b)

wherein $R_2$, $R_3$, $R_4$ and p are as previously defined.

7. The compound of claim 1, wherein A represents a fluorophore group selected from the group consisting of: Bodipy, and lissamine derivatives.

8. The compound of claim 1, wherein A represents one of the following groups:

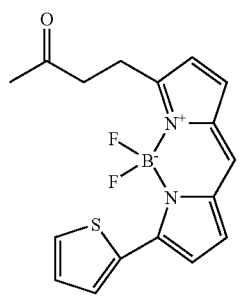

Bodipy derivative

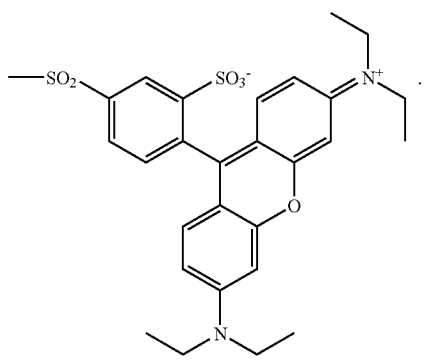

lissamine derivative

9. The compound of claim 1, corresponding to the following formula (III):

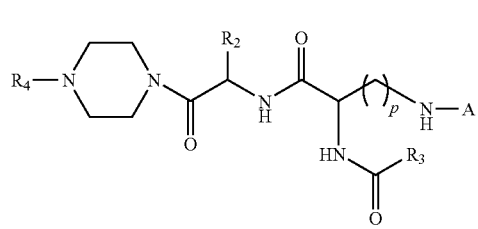

(III)

wherein:
$R_2$, $R_3$, $R_4$ and p are as previously defined,
the piperazine group is optionally substituted with one group selected from the group consisting of: an alkyl group comprising from 1 to 6 carbon atoms and an aromatic group, and
A represents a fluorophore group selected from the group consisting of: Bodipy, and lissamine derivatives.

10. The compound of claim 9, wherein p=4 and corresponding to the following formula:

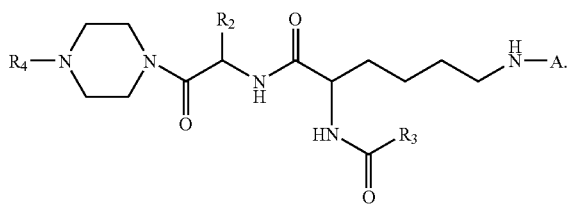

11. The compound of claim 9, corresponding to the following formula (III-a):

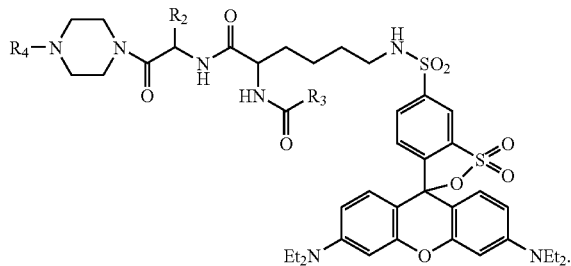

(III-a)

12. The compound of claim 1, corresponding to the following formula (IV):

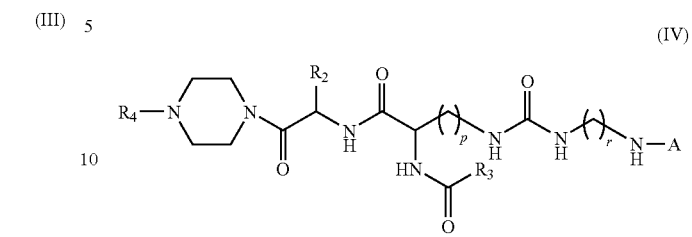

(IV)

wherein:
$R_2$, $R_3$, $R_4$, p and r are as previously defined,
the piperazine group is optionally substituted with one group selected from the group consisting of: an alkyl group comprising from 1 to 6 carbon atoms and an aromatic group, and
A represents a fluorophore group selected from the group consisting of: Bodipy, and lissamine derivatives.

13. The compound of claim 12, wherein p=4 and corresponding to the following formula:

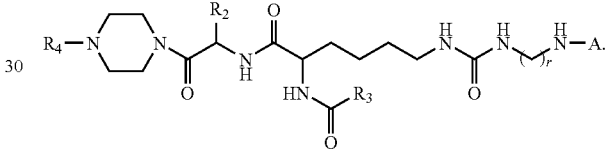

14. The compound of claim 12, wherein r=4 and corresponding to the following formula:

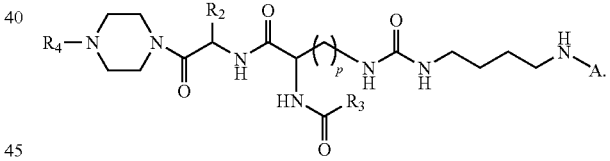

15. The compound of claim 12, wherein p and r are equal to 4 and corresponding to the following formula:

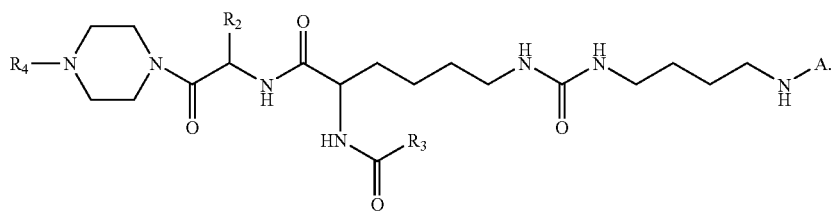

16. The compound of claim 12, corresponding to the following formula (IV-a):

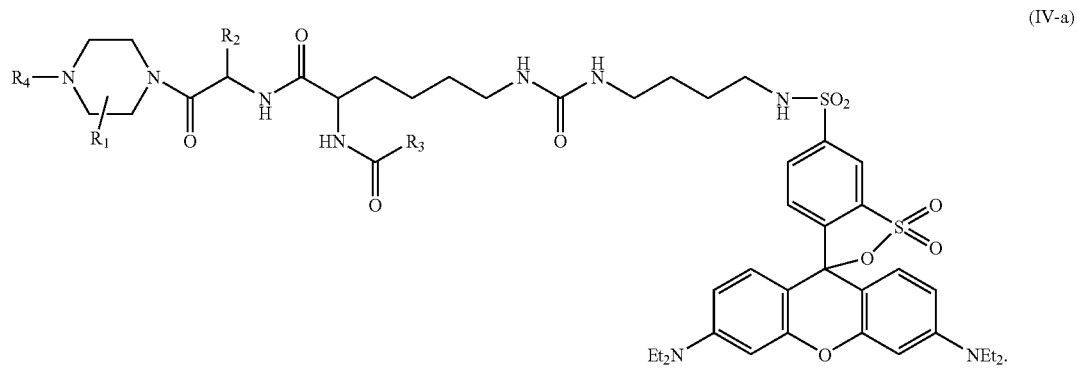

17. A collection comprising a plurality of compounds of formula (I) as defined in claim 1.

18. A collection comprising a plurality of compounds of formula (III-a) as defined in claim 11.

19. A collection comprising a plurality of compounds of formula (IV-a) as defined in claim 16.

20. A method for screening ligands of receptors no ligand of which is known or no useable ligand of which is known, said method comprising the following stages:
bringing a collection of traceable compounds of formula (I) according to claim 1, together with cells transfected by a construction containing the fusion of the sequence coding for a fluorescent protein with the nucleotide sequence coding for a receptor no ligand of which is known or no useable ligand of which is known, and the mixture of said cells and of said collection,
detecting the fluorescence of said mixture, by exciting said fluorescent protein and measuring the emission fluorescence of said fluorescent protein, and determining the fluorescence extinction percentage by comparing the emission fluorescence of said fluorescent protein to the average fluorescence of said fluorescent protein, the average fluorescence of said fluorescent protein being measured by control tests corresponding to the measurement of the fluorescence of the fluorescent protein in the absence of the collection of compounds, and
determining the compounds which produce a fluorescence extinction percentage of the fluorescent protein of at least 5% and identifying said compounds as ligand.

21. A method for the preparation on solid support of a compound of formula (I) of claim 1, comprising the following stages:
coupling a solid support of formula

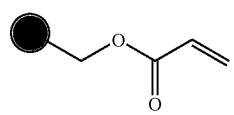

to a compound of formula

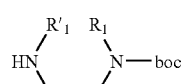

in order to obtain a compound of the following formula (1):

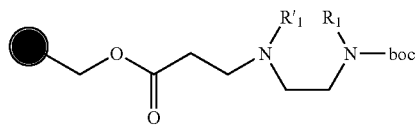

$R_1$ and $R'_1$ being as previously defined,
deprotecting the compound of formula (1) followed by coupling of said deprotected compound to the compound of formula

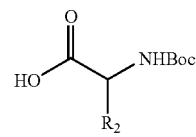

in order to obtain a compound of the following formula (2):

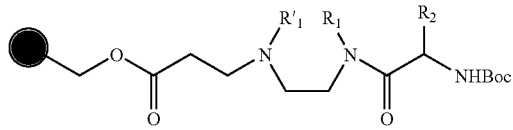

$R_2$ being as previously defined,
deprotecting the compound of formula (2) followed by coupling of said deprotected compound to the compound of formula

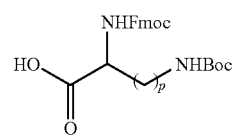

in order to obtain a compound of the following formula (3):

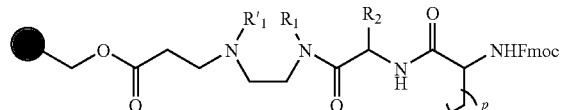

p being as previously defined,
deprotecting the Fmoc group of the compound of formula (3) followed by coupling of said deprotected compound to the compound $R_3COOH$ in order to obtain a compound of the following formula (4):

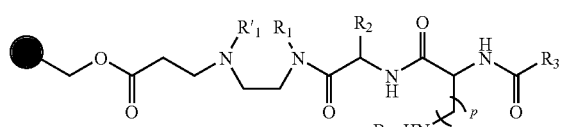

$R_3$ being as previously defined,
deprotecting the compound of formula (4) in order to obtain a compound of the following formula (5):

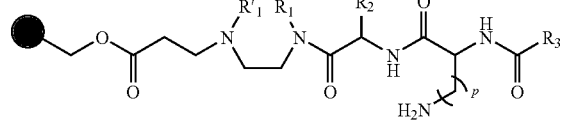

optionally, reacting the compound of formula (5) with p-nitrophenylchloroformate then with the diamine of formula

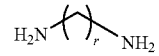

in order to obtain the compound of the following formula (6):

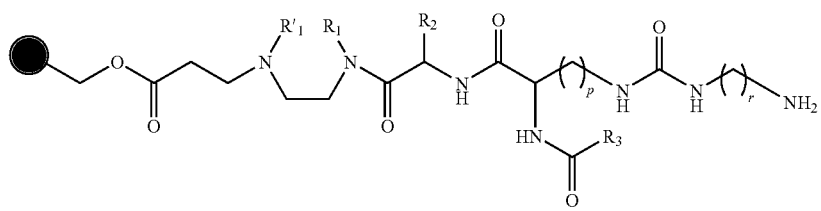

r being as previously defined,
reacting the compound of formula (5) or the compound of formula (6) with electrophilic tracers, in particular with A-Cl, in order to obtain the compound of the following formula (7):

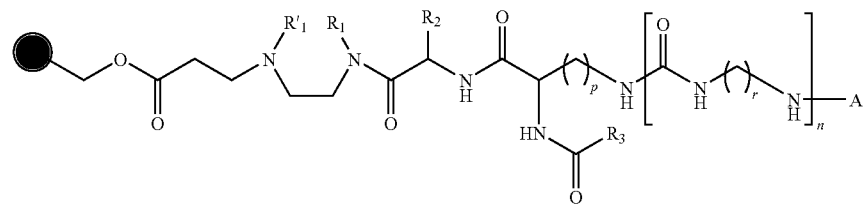

n being equal to 0 or 1,

A representing Bodipy in the form of activated acid or lissamine in the form of activated sulphonic acid, and cleaving the compound of formula (7) with the compound $R_4X$, $R_4$ being as defined above, and X representing a halogen atom, in particular I or Br, in order to obtain the compound of formula (I).

22. A method for the in vitro determination of ligands of receptors no ligand of which is known or no ligand of which is known that can be used to carry out specific affinity binding studies, comprising:

providing a collection of compounds corresponding to the following general formula (I):

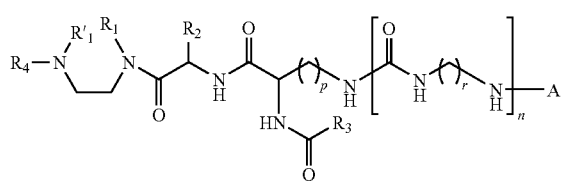

wherein:

n is equal to 0 or 1, p represents an integer varying from 1 to 6, r represents an integer varying from 1 to 12, $R_1$ and $R'_1$ represent independently of each other an atom or a group selected from the group consisting of: a hydrogen atom, an alkyl group comprising from 1 to 6 carbon atoms, and an aromatic group, or

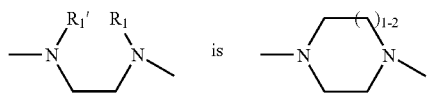

and the

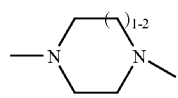

is optionally substituted with one group selected from the group consisting of: an alkyl group comprising from 1 to 6 carbon atoms and an aromatic group, $R_2$ represents a side chain of an amino acid or an amino acid derivative, $R_3$ represents a group derived from a carboxylic acid, carrying a basic entity, selected from the following groups:

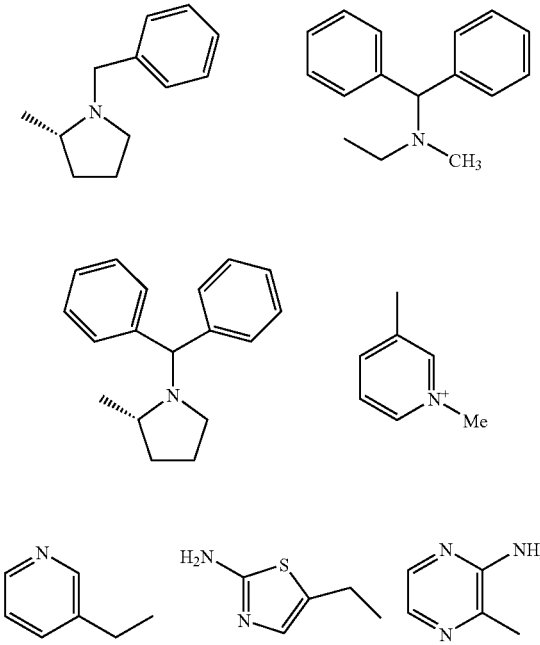

is selected from the group consisting of: an alkyl group comprising from 1 to 10 carbon atoms, a phenyl group substituted by an alkyl group comprising from 1 to 10 carbon atoms, and A represents a hydrogen atom, a protective group or a tracer group, in particular a fluorophore, a dye or a "quencher", and performing binding studies with said collection of compounds.

23. The method of claim 22, wherein the collection of compounds correspond to the following general formula (III-a)

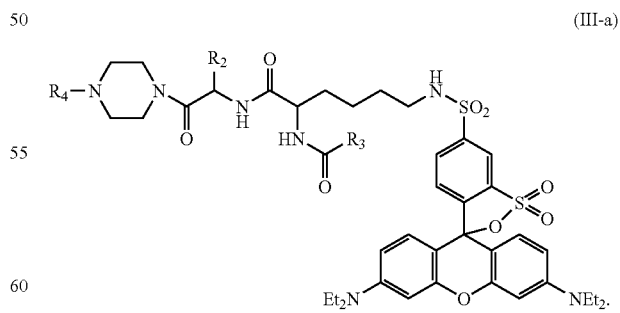

24. The method of claim 22, wherein the collection of compounds correspond to the following general formula (IV-a)

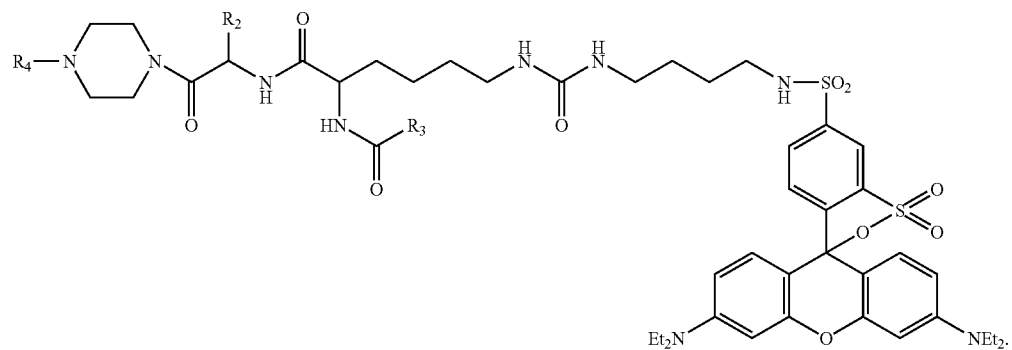
* * * * *

SEQUENCE LISTING

```
<160> NUMBER OF SEQ ID NOS: 8

<210> SEQ ID NO 1
<211> LENGTH: 34
<212> TYPE: DNA
<213> ORGANISM: Homo sapiens
<220> FEATURE:
<221> NAME/KEY: CDS
<222> LOCATION: (2)..(34)

<400> SEQUENCE: 1 g gcc ggg gcc ggg acc ccc tat ggc tgt att ggc                        34
  Ala Gly Ala Gly Thr Pro Tyr Gly Cys Ile Gly
   1               5                  10

<210> SEQ ID NO 2
<211> LENGTH: 11
<212> TYPE: PRT
<213> ORGANISM: Homo sapiens

<400> SEQUENCE: 2
```

-continued

```
Ala Gly Ala Gly Thr Pro Tyr Gly Cys Ile Gly
  1               5                  10

<210> SEQ ID NO 3
<211> LENGTH: 39
<212> TYPE: DNA
<213> ORGANISM: Homo sapiens
<220> FEATURE:
<221> NAME/KEY: CDS
<222> LOCATION: (1)..(39)

<400> SEQUENCE: 3 ctc gtt ctc gtt gga tca cac agc cat ttc atc agg atc              39
Leu Val Leu Val Gly Ser His Ser His Phe Ile Arg Ile
  1               5                  10

<210> SEQ ID NO 4
<211> LENGTH: 13
<212> TYPE: PRT
<213> ORGANISM: Homo sapiens

<400> SEQUENCE: 4

Leu Val Leu Val Gly Ser His Ser His Phe Ile Arg Ile
  1               5                  10

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accgccgccg ggatctcaga tctcggaaag ggtccctgg                       39

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer <400> SEQUENCE: 6
gcaggacgca ggctcgagtc agcattggcg ggaggg                          36

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtcggctgc ggccgcatgg gcctccgggc gct                             33

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccagggaccc tttccgagat ctgagatccc ggcggcggt                       39
```